(12) United States Patent
Rai et al.

(10) Patent No.: US 11,389,194 B2
(45) Date of Patent: Jul. 19, 2022

(54) SYSTEMS AND METHODS FOR VASCULAR ACCESS

(71) Applicant: SlipStream, LLC, Morgantown, WV (US)

(72) Inventors: Ansaar T. Rai, Morgantown, WV (US); Lakshmikumar Pillai, Morgantown, WV (US)

(73) Assignee: SlipStream, LLC, Morgantown, WV (US)

( * ) Notice: Subject to any disclaimer, the term of this patent is extended or adjusted under 35 U.S.C. 154(b) by 278 days.

(21) Appl. No.: 16/594,984

(22) Filed: Oct. 7, 2019

(65) Prior Publication Data

US 2020/0038057 A1    Feb. 6, 2020

Related U.S. Application Data

(63) Continuation of application No. 16/513,667, filed on Jul. 16, 2019, now Pat. No. 10,470,797.

(Continued)

(51) Int. Cl.
*A61B 17/34* (2006.01)
*A61M 25/01* (2006.01)
(Continued)

(52) U.S. Cl.
CPC ..... *A61B 17/3423* (2013.01); *A61M 25/0102* (2013.01); *A61M 25/0108* (2013.01);
(Continued)

(58) Field of Classification Search
CPC .............. A61M 25/0108; A61M 25/06; A61M 25/0102; A61M 2025/018;
(Continued)

(56) References Cited

U.S. PATENT DOCUMENTS 5,415,177 A    5/1995  Zadini et al.
6,068,638 A    5/2000  Makower
(Continued)

FOREIGN PATENT DOCUMENTS

JP    H07171158 A    7/1995

OTHER PUBLICATIONS

"TorFlex™ Transseptal Guiding Sheath", Baylis Medical Company Inc, downloaded from internet May 17, 2018 (3 pages).
(Continued)

*Primary Examiner* — Katherine M Shi
(74) *Attorney, Agent, or Firm* — Blair Walker IP Services, LLC

(57) ABSTRACT

A system for accessing arterial vasculature from a venous insertion site includes a first elongate tubular member, a second elongate tubular member configured to be disposed within a lumen of the first elongate tubular member, an elongate crossing member including a distal tip comprising a frusto-conical outer surface, and configured to be disposed within a first lumen of the second elongate tubular member, and a stylet configured to be disposed within a lumen of the elongate crossing member, wherein placement of the second elongate tubular member, elongate crossing member, and stylet together through the lumen of the first elongate tubular member does not substantially straighten a curved distal portion of the first elongate tubular member, and wherein the elongate crossing member and stylet are removable from the first lumen of the second elongate tubular member when it is within the lumen of the first elongate tubular member with at least its distal end extending out of the first elongate tubular member.

20 Claims, 14 Drawing Sheets

Related U.S. Application Data

(60) Provisional application No. 62/699,037, filed on Jul. 17, 2018.

(51) Int. Cl.
*A61M 25/06* (2006.01)
*A61B 17/32* (2006.01)
*A61B 17/00* (2006.01)

(52) U.S. Cl.
CPC ... *A61M 25/06* (2013.01); *A61B 2017/00278* (2013.01); *A61B 2017/00778* (2013.01); *A61B 2017/320044* (2013.01); *A61B 2017/3425* (2013.01)

(58) Field of Classification Search
CPC ...... A61M 2025/0197; A61M 25/0082; A61M 25/01; A61M 25/0194; A61M 2025/0095; A61M 2025/0681; A61M 2025/09125; A61M 25/0053; A61M 25/0068; A61M 25/008; A61M 25/0141; A61M 25/0152; A61M 25/0662; A61B 17/3423; A61B 2017/00278; A61B 2017/3425; A61B 2017/00778; A61B 2017/320044; A61B 2017/22095; A61B 17/34

See application file for complete search history.

(56) References Cited

U.S. PATENT DOCUMENTS

| | | |
|---|---|---|
| 6,190,353 B1 | 2/2001 | Mawoker et al. |
| 6,491,707 B2 | 12/2002 | Makower et al. |
| 6,511,458 B2 | 1/2003 | Milo et al. |
| 6,544,230 B1 | 4/2003 | Flaherty et al. |
| 6,561,998 B1 | 5/2003 | Roth et al. |
| 6,572,593 B1 | 6/2003 | Daum |
| 6,616,675 B1 | 9/2003 | Evard et al. |
| 6,660,024 B1 | 12/2003 | Flaherty et al. |
| 6,685,716 B1 | 2/2004 | Flaherty et al. |
| 6,692,466 B1 | 2/2004 | Chow et al. |
| 6,694,983 B2 | 2/2004 | Wolf et al. |
| 6,709,444 B1 | 3/2004 | Makower |
| 6,726,677 B1 | 4/2004 | Flaherty et al. |
| 6,994,693 B2 | 2/2006 | Tal |
| 7,273,469 B1 | 9/2007 | Chan et al. |
| 8,568,435 B2 | 10/2013 | Pillai et al. |
| 8,753,366 B2 | 6/2014 | Makower et al. |
| 9,220,874 B2 | 12/2015 | Pillai et al. |
| 9,511,214 B2 | 12/2016 | Pillai |
| 9,623,217 B2 | 4/2017 | Pillai |
| 9,877,833 B1 | 1/2018 | Bishop et al. |
| 2002/0169377 A1 | 11/2002 | Khairkhahan et al. |
| 2004/0181150 A1 | 9/2004 | Evans et al. |
| 2005/0149097 A1 | 7/2005 | Regnell et al. |
| 2006/0135962 A1 | 6/2006 | Kick et al. |
| 2006/0167416 A1 | 6/2006 | Mathis et al. |
| 2007/0167801 A1 | 6/2007 | Webler et al. |
| 2007/0265516 A1 | 11/2007 | Wang |
| 2009/0093670 A1 | 4/2009 | Annest et al. |
| 2009/0171276 A1 | 7/2009 | Bednarek et al. |
| 2009/0182268 A1 | 7/2009 | Thielen et al. |
| 2009/0222083 A1 | 9/2009 | Nguyen et al. |
| 2009/0287182 A1 | 11/2009 | Bishop et al. |
| 2010/0185172 A1 | 7/2010 | Fabro |
| 2010/0211131 A1 | 8/2010 | Williams et al. |
| 2010/0217117 A1 | 8/2010 | Glossop et al. |
| 2010/0249491 A1 | 9/2010 | Farnan et al. |
| 2010/0331697 A1 | 12/2010 | Webler et al. |
| 2011/0270191 A1 | 11/2011 | Paul et al. |
| 2011/0295206 A1 | 12/2011 | Gurley |
| 2012/0136247 A1 | 5/2012 | Pillai |
| 2013/0123620 A1 | 5/2013 | Tekulve et al. |
| 2013/0245533 A1 | 9/2013 | Kahn et al. |
| 2013/0274784 A1* | 10/2013 | Lenker ............ A61B 17/32053 606/185 |
| 2014/0121749 A1 | 5/2014 | Roeder |
| 2014/0257203 A1 | 9/2014 | Favier et al. |
| 2014/0277054 A1 | 9/2014 | McNamara et al. |
| 2015/0141836 A1 | 5/2015 | Naumann et al. |
| 2016/0193459 A1 | 7/2016 | Guadiani |
| 2016/0361088 A1 | 12/2016 | Maguire et al. |
| 2016/0374710 A1 | 12/2016 | Sinelnikov et al. |
| 2017/0157375 A1 | 6/2017 | Heilman et al. |
| 2017/0231563 A1 | 8/2017 | Tsamir et al. |
| 2017/0245885 A1 | 8/2017 | Lenker |
| 2017/0296798 A1 | 10/2017 | Kume et al. |
| 2017/0326354 A1 | 11/2017 | Westlund et al. |
| 2018/0116522 A1 | 5/2018 | Brenneman et al. |
| 2018/0161550 A1 | 6/2018 | Pillai et al. |
| 2018/0161551 A1 | 6/2018 | Pillai |

OTHER PUBLICATIONS

Feldman, T., Fisher, W., "Transseptal Puncture," in Problem Oriented Approaches in Interventional Cardiology, 2007, pp. 203-218, ed. Colombo, A., Taylor and Francis Group, LLC, Boca Raton, USA.

Kar, S., "Transseptal Puncture Technique," Cedars Sinai Medical Center, Los Angeles, USA, downloaded from internet May 17, 2018 (25 pages).

Rainbow, R., Raftery, E., Oakley, C., "Improved Design for a Transseptal Needle," British Hearth Journal, Aug. 1967, pp. 394-395, vol. 29, British Cardiovascular Society, London, UK.

Wang, Y., Xue, Y., Mohanty, P., Natale, A., Li, L., Wu, W., Zhu, C., Liu, H., Zhong, G., Zhu, L., Zeng, Z., Wang, D., "Dilator method and needle method for atrial transseptal puncture: a retrospective study from a cohort of 4443 patients," Europace, 2012, pp. 1450-1456, vol. 14, European Society of Cardiology, Sophia Antipolis, France.

* cited by examiner

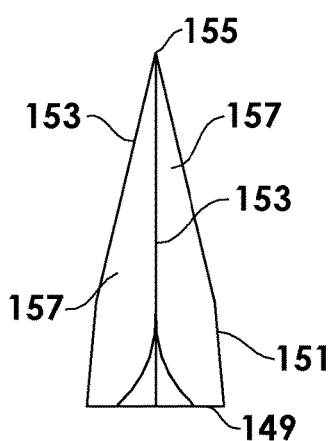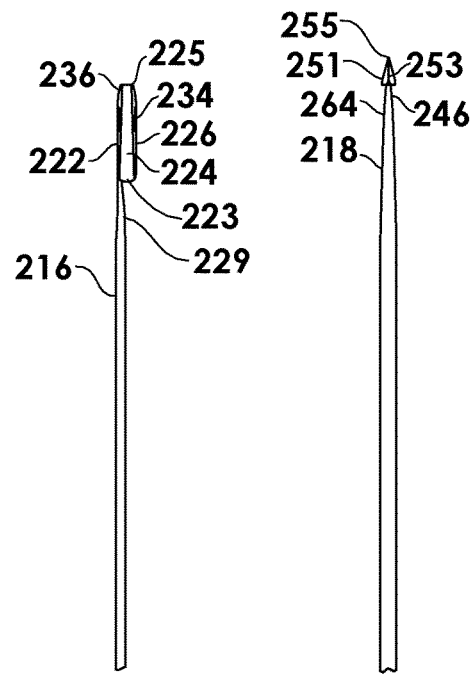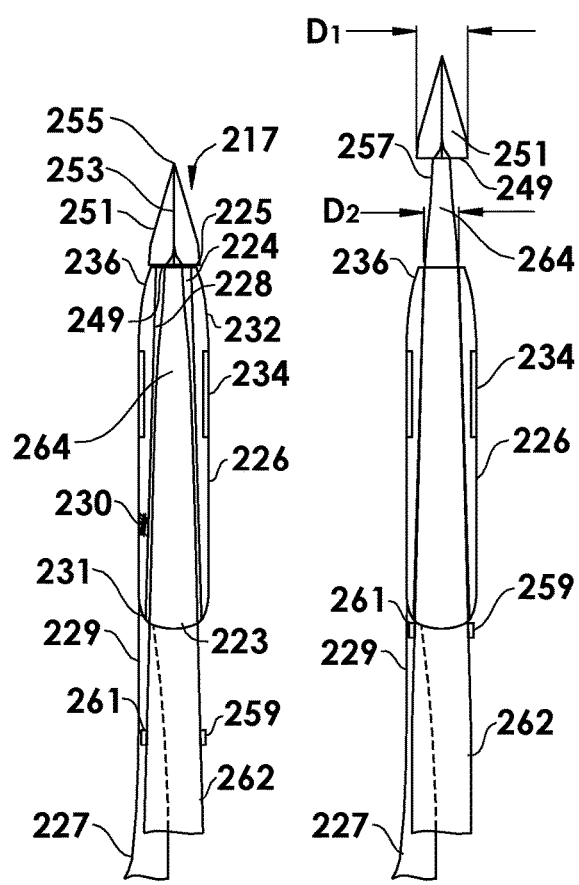
FIG. 17
FIG. 19
FIG. 20
FIG. 18

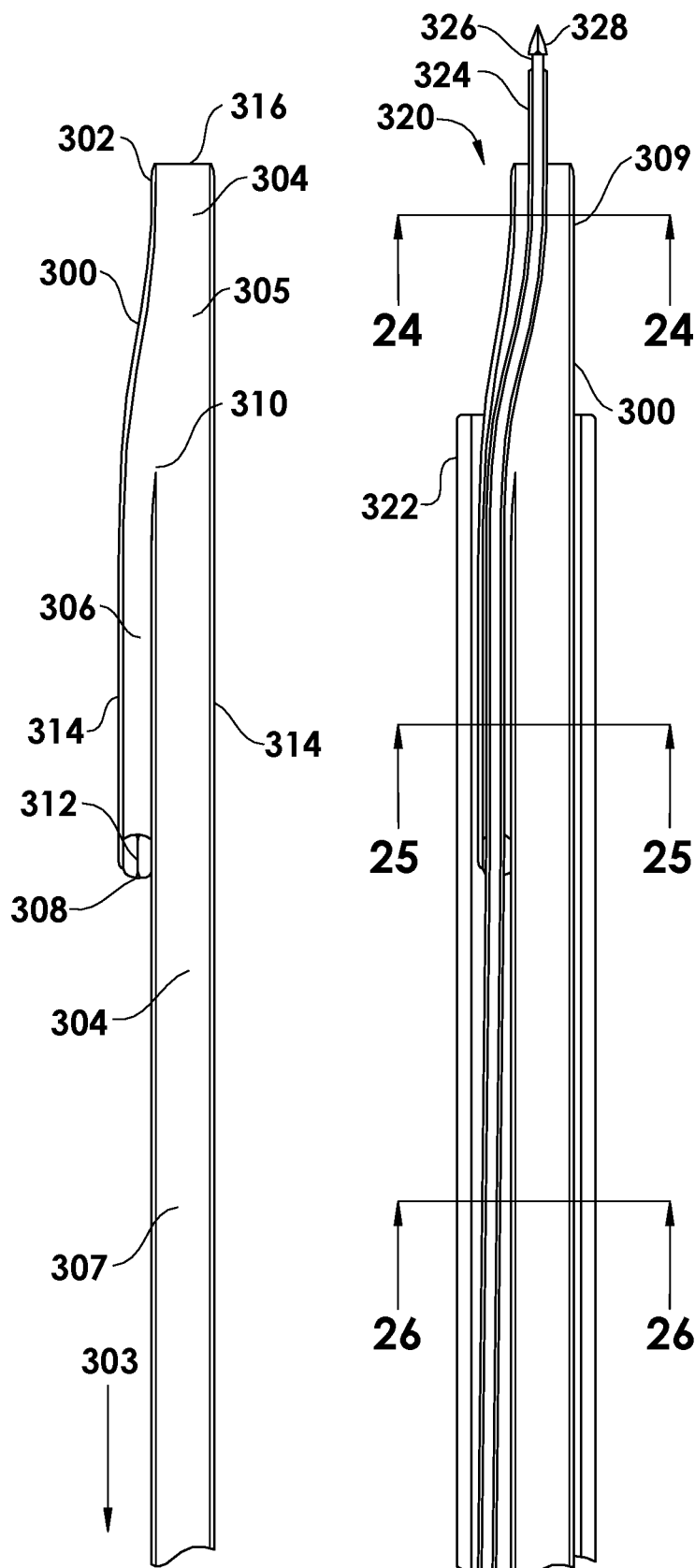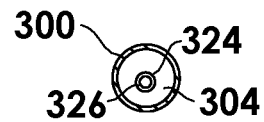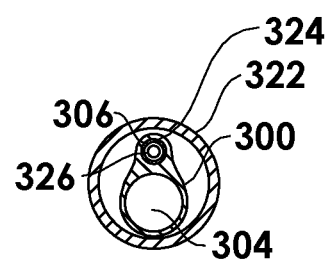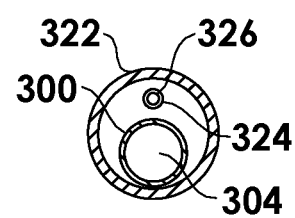
FIG. 22  FIG. 23  FIG. 24  FIG. 25  FIG. 26

SYSTEMS AND METHODS FOR VASCULAR ACCESS

INCORPORATION BY REFERENCE TO ANY PRIORITY APPLICATIONS

This application is a continuation of U.S. patent application Ser. No. 16/513,667, filed on Jul. 16, 2019, now U.S. Pat. No. 10,470,797, which claims the benefit of priority to U.S. Provisional App. No. 62/699,037, filed on Jul. 17, 2018, both of which are incorporated by reference in their entirety herein for all purposes. Priority is claimed pursuant to 35 U.S.C. § 120 and 35 U.S.C. § 119.

BACKGROUND OF THE INVENTION

Field of the Invention

The field of the invention generally relates to systems and methods for vascular access in patients having vascular disease.

SUMMARY OF THE INVENTION

In a first embodiment of the present disclosure, a system for accessing arterial vasculature from a venous insertion site includes a first elongate tubular member having a proximal end, a distal end, a lumen extending therebetween, and a curved distal portion at or adjacent the distal end, a second elongate tubular member configured to be disposed within the lumen of the first elongate tubular member for two-way longitudinal movement therein, the second elongate tubular member having a proximal end, a distal end, and a first lumen extending therebetween, an elongate crossing member configured to be disposed within the first lumen of the second elongate tubular member for two-way longitudinal movement therein, and having a proximal end, a distal end, and a lumen extending between the distal end and an orifice proximal to the distal end, the distal end of the elongate crossing member including a distal tip comprising a frusto-conical outer surface, and a stylet configured to be disposed within the lumen of the elongate crossing member for two-way longitudinal movement therein, the stylet having a proximal end and a distal end including a puncturing tip configured to penetrate a venous wall and an arterial wall adjacent the venous wall, wherein placement of the second elongate tubular member, the elongate crossing member, and the stylet together through the lumen of the first elongate tubular member at the curved distal portion does not substantially straighten the curved distal portion, and wherein the elongate crossing member and the stylet are removable from the first lumen of the second elongate tubular member when the second elongate tubular member is within the lumen of the first elongate tubular member with at least the distal end of the second elongate tubular member extending out of the distal end of the first elongate tubular member.

In another embodiment of the present disclosure, a method for accessing arterial vasculature from a venous insertion site includes providing a system for accessing arterial vasculature from a venous insertion site, the system including a first elongate tubular member having a proximal end, a distal end, a lumen extending therebetween, and a curved distal portion at or adjacent the distal end, a second elongate tubular member configured to be disposed within the lumen of the first elongate tubular member for two-way longitudinal movement therein, the second elongate tubular member having a proximal end, a distal end, and a first lumen extending therebetween, an elongate crossing member configured to be disposed within the first lumen of the second elongate tubular member for two-way longitudinal movement therein, and having a proximal end, a distal end, and a lumen extending between the distal end and an orifice proximal to the distal end, the distal end of the elongate crossing member including a distal tip comprising a frusto-conical outer surface, and a stylet configured to be disposed within the lumen of the elongate crossing member for two-way longitudinal movement therein, the stylet having a proximal end and a distal end including a puncturing tip configured to penetrate a venous wall and an arterial wall adjacent the venous wall, wherein placement of the second elongate tubular member, the elongate crossing member, and the stylet together through the lumen of the first elongate tubular member at the curved distal portion does not substantially straighten the curved distal portion, and wherein the elongate crossing member and the stylet are removable from the first lumen of the second elongate tubular member when the second elongate tubular member is within the lumen of the first elongate tubular member with at least the distal end of the second elongate tubular member extending out of the distal end of the first elongate tubular member, placing the distal end of the first elongate tubular member into a vein from an external puncture site, advancing the first elongate tubular member such that the distal end of the first elongate tubular member is positioned adjacent a wall portion of an internal jugular vein, advancing the stylet such that the puncturing tip of the stylet penetrates the wall portion of the internal jugular vein and penetrates an adjacent wall portion of a common carotid artery, advancing the distal end of the elongate crossing member into the common carotid artery through an opening created by the penetration of the puncturing tip of the stylet, advancing the second elongate tubular member into the common carotid artery; removing the elongate crossing member and the stylet from the second elongate tubular member, and performing an interventional procedure through the second elongate tubular member.

In yet another embodiment of the present disclosure, a system for accessing arterial vasculature from a venous insertion site includes a first elongate tubular member having a proximal end, a distal end, a lumen extending therebetween, and a curved distal portion at or adjacent the distal end, a second elongate tubular member configured to be disposed within the lumen of the first elongate tubular member for two-way longitudinal movement therein, the second elongate tubular member having a proximal end, a distal end, and a lumen extending therebetween, an elongate crossing member configured to be disposed within the lumen of the second elongate tubular member for two-way longitudinal movement therein, and having a proximal end, a distal end, and a lumen extending between the distal end and an orifice proximal to the distal end, the distal end of the elongate crossing member comprising a frusto-conical outer surface, a stylet configured to be disposed within the lumen of the elongate crossing member for two-way longitudinal movement therein, the stylet having a proximal end and a puncturing tip configured to penetrate a venous wall and an arterial wall adjacent the venous wall, and a connector configured to facilitate controlled longitudinal movement of the stylet in relation to the first elongate tubular member, wherein the elongate crossing member and the stylet are removable from the lumen of the second elongate tubular member when the second elongate tubular member is within the lumen of the first elongate tubular member with at least the distal end of the second elongate tubular member extending out of the distal end of the first elongate tubular member.

In still another embodiment of the present disclosure, a system for accessing arterial vasculature from a venous insertion site includes a first elongate tubular member having a proximal end, a distal end, a lumen extending therebetween, and a curved distal portion at or adjacent the distal end, a second elongate tubular member configured to be disposed within the lumen of the first elongate tubular member for two-way longitudinal movement therein, the second elongate tubular member having a proximal end, a distal end, a first lumen extending therebetween, and a second lumen communicating with the first lumen at a distal portion of the second elongate tubular member and having an exit port proximal to the distal portion, an elongate crossing member configured to be disposed within the second lumen of the second elongate tubular member for two-way longitudinal movement therein, and having a proximal end, a distal end, and a lumen extending between the distal end and an orifice proximal to the distal end, the distal end of the elongate crossing member comprising a frusto-conical outer surface, and a stylet configured to be disposed within the lumen of the elongate crossing member for two-way longitudinal movement therein, the stylet having a proximal end and a puncturing tip configured to penetrate a venous wall and an arterial wall adjacent the venous wall, wherein the second elongate tubular member is removable in a proximal direction over the elongate crossing member and the stylet.

BRIEF DESCRIPTION OF THE DRAWINGS

FIG. 17 is a detail view of the puncture member of the stylet of FIG. 1.

FIG. 18 is a partial sectional view of a stylet and a stylet sheath/dilator according to an alternative embodiment of the present disclosure.

FIG. 19 is a partial sectional view of the stylet and stylet sheath/dilator of FIG. 18 in a first configuration.

FIG. 20 is a partial sectional view of the stylet and stylet sheath/dilator of FIG. 18 in a second configuration.

FIG. 22 is a sectional view of an alternative guiding catheter according to an embodiment of the present disclosure.

FIG. 23 is a sectional view of a system for accessing arterial vasculature from a venous insertion site incorporating the guiding catheter of FIG. 22, according to an embodiment of the present disclosure.

FIG. 24 is a cross-sectional view of FIG. 23 taken at line 24.

FIG. 25 is a cross-sectional view of FIG. 23 taken at line 25.

FIG. 26 is a cross-sectional view of FIG. 23 taken at line 26.

DETAILED DESCRIPTION OF THE ILLUSTRATED EMBODIMENTS

Figure 1:
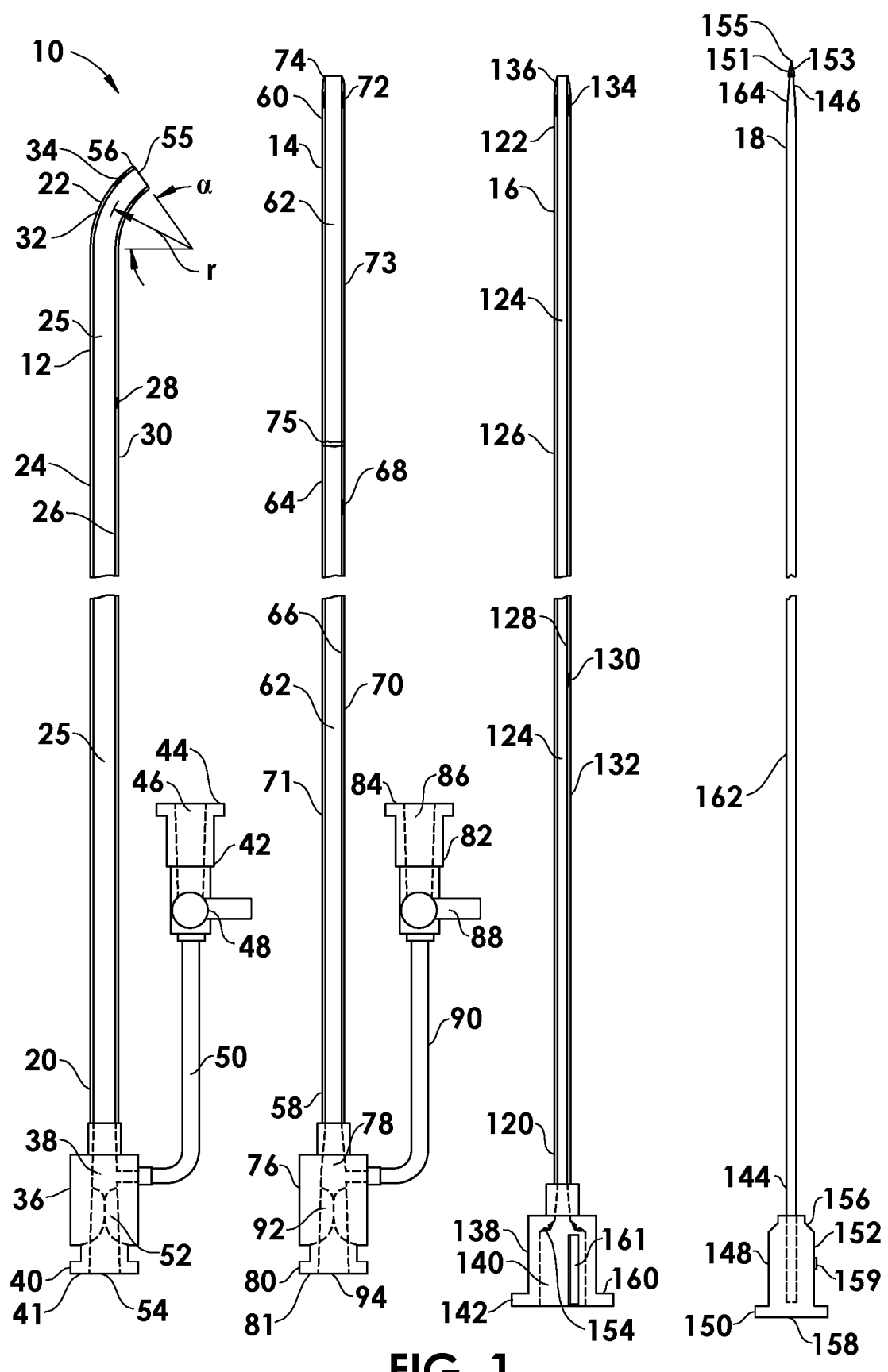
FIG. 1 is a partial sectional view of a system for accessing arterial vasculature from a venous insertion site, according to an embodiment of the present disclosure.

The present disclosure relates to systems for accessing arterial vasculature. A large variety of interventional procedures are commonly performed within the internal carotid arteries and the cerebral vasculature, including the middle cerebral arteries, the anterior cerebral arteries, the posterior cerebral arteries, the anterior communicating artery, the posterior communicating arteries, and the basilar artery. Traditionally, a sheath is placed via Seldinger technique or by cutdown into the femoral artery in the area of the groin of the patient. A guiding catheter is then inserted through the descending aorta and into the aortic arch. From the aortic arch, the left or right common carotid arteries may be accessed, leading to the left or right internal carotid arteries. Additionally, the left or right subclavian arteries can be accessed, leading to the left or right vertebral arteries and the basilar artery. The left and right internal carotid arteries and the basilar artery access what is known as the Circle of Willis.

The current minimally-invasive cerebrovascular interventions can be broadly categorized into ischemic and hemorrhagic categories. Interventions in the ischemic category include endovascular treatment of acute ischemic stroke and the treatment of intra- and extra-cranial atherosclerotic disease. Common interventional procedures for acute stroke intervention include the delivery of thrombolytic drugs such as tissue plasminogen activator (tPA) through catheters, often called microcatheters. Mechanical thrombectomy may be performed with thrombectomy catheters having a clot disrupting element, or aspiration of thrombus may be performed through the lumen of an aspiration catheter. In some cases, stents may be delivered to maintain an artery in an open position. Other common interventional procedures may include angioplasty or stenting of the internal carotid arteries, or the common carotid arteries, which may become thrombosed, or may become stenosed with atherosclerotic material. In some cases, thrombosis occurs directly at a site of atherosclerotic stenosis. The dominant procedure in the hemorrhagic category is endovascular treatment of cerebral aneurysms. A wide array of embolization procedures may also be performed, to fill or close aneurysms or malformations, including cerebral aneurysms, arteriovenous malformations (AVMs), or other malformations. These include, but are not limited to embolic coils, injected embolic materials, or braided globular or tubular implants. Other embolization procedures are performed to stop chromic nosebleeds, or to impede the blood flow to tumors. Thus, the ability to access the arterial vasculature in the neck and head area has critical importance.

Angioplasty and stenting of carotid arteries, either in combination or separately, are commonly performed in a significant number of patients. Restoring blood flow and maintaining blood flow through carotid arteries is critical, as the carotids are responsible for a large portion of the blood supply to the brain. These procedures may be performed to treat stroke or to prevent stroke.

As the field has matured, an increasing number of these pathologies are being approached via endovascular interventions, at times requiring deeper and more complex delivery of devices within or adjacent the brain, or generally in the head and neck area. In addition, whether a procedure is to be performed within a distal (e.g., cerebral) vessel, or in a carotid artery, it is often desirable to have good backup support by an access catheter, which allows better delivery of a therapeutic catheter passed therethrough. A durable access platform can be a key success-determining factor in complex interventions. Even though there has been much progress in the development of access tools in the form of guiding catheters (guide catheters), intermediate catheters, microcatheters, and microwires, the one theme that has remained consistent is their delivery through the arterial system. This provides the most direct route to a target artery, aneurysm, or malformation, but the arterial system between the access point and the target point can also be fraught with challenges, anatomical or otherwise. The arterial system is prone to the effects of inflammation, systemic illnesses and aging—the same risk factors implicated in cerebrovascular pathologies such as stroke and aneurysms. Many patients, have peripheral disease, that may preclude the standard access via the femoral arteries. Femoral or iliac artery atherosclerosis (e.g., plaque), or femoral or iliac artery tortuosity, or similar subclavian morphology or disease, can make it difficult or impossible to track the desired catheters and/or guidewires to the aortic arch, and to the target vessels. The distal end of a sheath or guiding catheter may not be able to pass a significantly curved vessel or a significantly stenosed or even occluded vessel. Tortuosity from the aorto-iliac level to the aortic arch and the origin of the great vessels can translate into a hostile route and is a major factor complicating stable and safe access to the neurovascular space. The current limitation of a disease-prone arterial access pathway constitutes an unmet need for simpler, safe, and stable access.

Unstable or inconsistent access can result in failed procedures for the treatment of acute ischemic stroke, cervical and intracranial atherosclerotic disease, cerebral aneurysms, or other malformations or maladies. Acute stroke interventions are often time-sensitive, and thus unstable access has been cited as one of the major factors for procedural failures and poor outcomes. Attempts to overcome these challenges can involve complex and time consuming multi-axial catheter constructs and may even require direct carotid access techniques. Percutaneous carotid access may provide a more direct route to the cerebral vasculature but is limited by two major factors: ease of use and safety. In terms of ease of use, many current neurovascular access devices are designed with a transfemoral access in mind, Interventionalists performing the procedures have often been trained on and are accustomed to using transfemoral access. Femoral access not only provides a more comfortable operating space but also moves the operator away from the radiation field centered over the head, an important point for a person planning to make a career of performing these types of procedures. The configuration of the angiography equipment, layout of the operating suite, and anesthesia setup are optimized for operating from the groin of the patient. Direct carotid access, on the other hand, puts the operator closer to the radiation field and makes manipulation of catheters and wires dangling outside the body more challenging. Direct access is associated with higher complication rates and also creates new challenges when performing closure of the access site.

Access using the radial artery has gained popularity, to avoid the femoral and iliac vessels, and to accelerate patient post-procedural ambulation. However, the typically smaller diameter of the radial artery can often preclude the use of certain access systems or catheter systems having larger diameters. Like the femoral and iliac arteries, the radial arteries can also present morphological or disease-caused access challenges.

The venous system, in contrast, is not affected in the same way by systemic illnesses and can offer a potential large capacitance conduit to the intracranial circulation. If the venous system can be used to access the cervical or intracranial arterial circulation, it will bypass the diseased and/or tortuous aorto-iliac vasculature, the hostile aortic arch and tortuous (curvy) proximal great vessels. This can reduce procedure times, and also potentially reduce thromboembolic complications that can happen as a result of traversing a diseased atherosclerotic artery.

Figure 2:
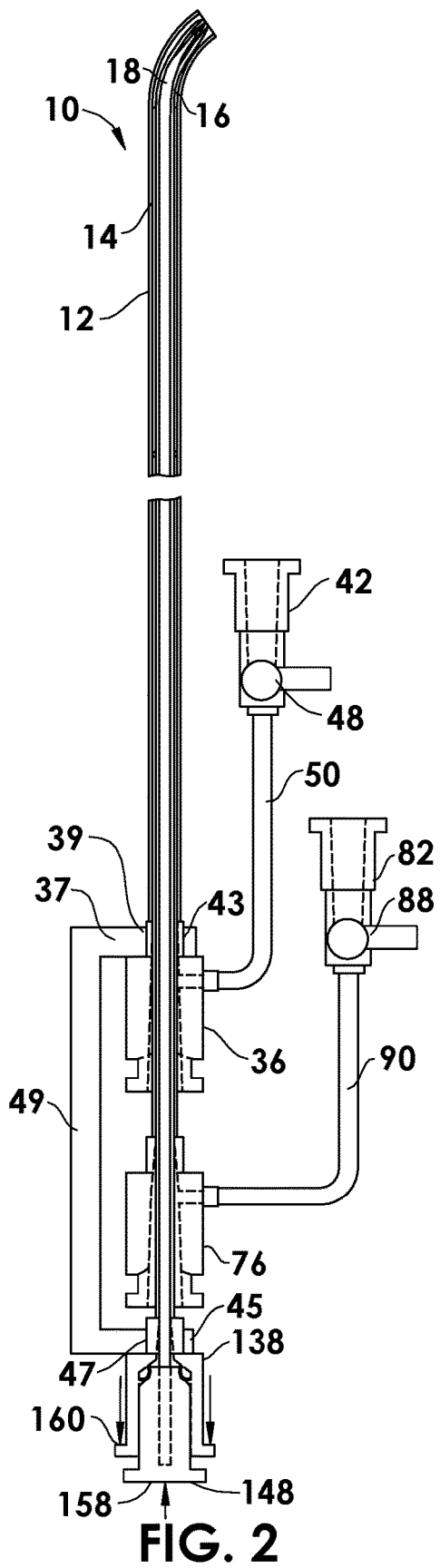
FIG. 2 is a partial sectional view of the system for accessing arterial vasculature from a venous insertion site of FIG. 1 in an assembled configuration, according to an embodiment of the present disclosure.

FIG. 1 illustrates a system for accessing arterial vasculature from a venous insertion site 10 comprising a curved outer sheath 12, a guiding catheter 14, a stylet sheath/dilator 16, and a stylet 18. As illustrated in FIG. 2, the stylet 18 is configured to be placed within the stylet sheath/dilator 16, the stylet 18 and stylet sheath/dilator 16 are configured to be placed within the guiding catheter 14, and the stylet 18, stylet sheath/dilator 16, and guiding catheter 14 are configured to be placed within the curved outer sheath 12. Returning to FIG. 1, the curved outer sheath 12 comprises a proximal end 20, a distal end 22, and a lumen 25 extending between the proximal end 20 and the distal end 22. The curved outer sheath 12 comprises a tubular body 24 which may be made from a variety of materials, including polymeric materials such as PEBAX® (polyether block amide), Nylon, and polyurethane. The tubular body 24 may include a composite design, such as a lubricious inner layer 26 comprising PTFE, ETFE, or other fluoropolymer, a braided, coil-reinforced, or machined hypo tube intermediate layer 28, and an outer material 30 comprising polymeric materials such as PEBAX® (polyether block amide), Nylon, and polyurethane. The intermediate layer 28 may comprise stainless steel, nickel-titanium alloy, or other metallic material, and may extend from the proximal end 20 to the distal end 22, or from the proximal end 20 to an intermediate location, proximal to the distal end 22. The curved outer sheath 12 may have a continuous outer diameter, or in other embodiments, may taper at the distal end 22, for example, to a smaller diameter. In some embodiments, the curved outer sheath 12 has an outer diameter of between about 0.105 inch and about 0.155 inch, or between about 0.119 inch and about 0.145 inch, or between about 0.130 inch and about 0.145 inch. In some embodiments, the lumen 25 of the curved outer sheath 12 has a diameter (or a maximum transverse dimension, if not circular) of between about 0.080 inch and about 0.140 inch, or between about 0.095 inch and about 0.122 inch, or between about 0.108 inch and about 0.122 inch. In some embodiments, the length of the curved outer sheath 12 is between the proximal end 20 and the distal end 22 is between about 55 cm and about 80 cm, or between about 60 cm and about 75 cm, or between about 65 cm and about 70 cm.

At the distal end 22 of the curved outer sheath 12 is a curved portion 32 which is configured to provide targeted entry of the stylet 18 through a venous wall and an adjacent arterial wall, as will be described further herein. In one particular embodiment, the curved portion 32 is configured to provide targeted entry of the stylet through the wall of an internal jugular vein and the adjacent wall of a common carotid artery. In this embodiment, the curved portion 32 has a radius of curvature r of between about 0.50 cm and about 2.75 cm, or between about 0.75 cm and about 2.50 cm, or between about 1.00 cm and about 2.25 cm. The curved portion 32 sweeps over an arc having an angle α of between about 30° and about 110°, or between about 30° and about 80°, or between about 40° and about 60°. The curved portion 32 is configured to have enough flexibility so that it can sufficiently straighten to allow insertion through a puncture in the skin and vein and into the vein. However, the curved portion 32 is also configured to have curve retention such that placement of distal portions of the guiding catheter 14, stylet sheath/dilator 16, and stylet 18 within the lumen 25 does not substantially straighten the curved portion 32. Curve retention of this nature is configured to be operative at human body temperature (e.g., 37° C.).

A radiopaque marker 34 may be coupled to the distal end 22 of the curved outer sheath 12 by adhesive or epoxy bonding, swaging, printing, coating, sputtering, ion implantation, or other methods. The radiopaque marker 34 allows for visualization of the distal end 22 of the curved outer sheath 12 by x-ray or fluoroscopy, and the radiopaque maker 34 may comprise platinum, iridium, tantalum, rhenium, tungsten, gold, or an alloy of these materials with each other or with other materials. The distal end 22 of the curved outer sheath 12 may have a taper or fillet 56, for example, to aid insertion through a skin and venous wall puncture. The curved outer sheath 12 includes a proximal hub 36 having an inner cavity 38 in fluid communication with the lumen 25, and having an optional female luer connector 40 at its proximal end 41. A sideport 42 having a female luer connector 44, a lumen 46 and a stopcock 48 is coupled via an extension tube 50 to the proximal hub 36. The proximal hub 36 includes a valve 52 configured to seal around the shafts of any other component (e.g., the guiding catheter 14) that is placed through the inner cavity 38 and lumen 25. The valve 52 is also configured to assure that, even without any device placed through the inner cavity 38 or lumen 25, liquid injected through the lumen 46 of the sideport 42 and the extension tube 50 passes through the lumen 25 of the curved outer sheath 12, and not out the orifice 54 of the proximal hub 36. In some embodiments, the valve 52 is configured to seal the lumen 25 of the curved outer sheath 12 from venous pressure, such as systolic superior vena cava pressure, systolic inferior vena cava pressure, or systolic internal jugular vein pressure. In some embodiments, a higher-pressure valve 52 is desired, and the valve 52 is configured to seal the lumen 25 of the curved outer sheath 12 from arterial pressure, such as systolic common carotid pressure, or systolic cerebral artery pressure. This could be useful if a distal end 22 of the curved outer sheath 12 was placed through a puncture created between a vein and an adjacent artery, which would thus expose the lumen 25 to higher arterial pressure via a distal orifice 55. The distal end 22 of the curved outer sheath 12 may alternatively have a hydrophilic coating, silicone coating, or other lubricious coating, to aid insertion into and/or tracking through blood vessels. The composite structure of the tubular body 24 allows for sufficient torqueability, to allow the curved outer sheath 12 to be torqued with close to a one-to-one response, such that the curved portion 32 can be accurately aimed at a desired target site on a venous wall.

The guiding catheter 14 comprises a proximal end 58, a distal end 60, and a lumen 62 extending between the proximal end 58 and the distal end 60. The guiding catheter 14 comprises a tubular body 64 which may be made from a variety of materials, including polymeric materials such as PEBAX® (polyether block amide), Nylon, and polyurethane. The tubular body 64 may include a composite design, such as a lubricious inner layer 66 comprising PTFE, ETFE, or other fluoropolymer, a braided, coil-reinforced, or machined hypo tube intermediate layer 68, and an outer material 70 comprising polymeric materials such as PEBAX® (polyether block amide), Nylon, and polyurethane. The intermediate layer 68 may comprise stainless steel, nickel-titanium alloy, or other metallic material, and may extend from the proximal end 58 to the distal end 60, or from the proximal end 58 to an intermediate location, proximal to the distal end 60. The guiding catheter 14 may have a continuous outer diameter, or in other embodiments, may taper at the distal end 60, for example, to a smaller diameter. In some embodiments, the guiding catheter 14 has an outer diameter of between about 0.070 inch and about 0.110 inch, or between about 0.070 inch and about 0.100 inch, or between about 0.075 inch and about 0.095 inch. In some embodiments, the lumen 62 of the guiding catheter 14 has a diameter (or a maximum transverse dimension, if not circular) of between about 0.060 inch and about 0.075 inch, or between about 0.065 inch and about 0.070 inch. In some embodiments, the length of the guiding catheter 14 is between the proximal end 58 and the distal end 60 is between about 90 cm and about 135 cm, or between about 100 cm and about 125 cm, or between about 105 cm and about 120 cm.

The tubular body 64 may include a proximal portion 71 and a distal portion 73, wherein the distal portion 73 is more flexible than the proximal portion 71, such that the proximal portion 71 is particularly configured for pushing and the distal portion is particularly configured for tracking a curvaceous blood vessel. The proximal portion 71 may be connected to the distal portion 73 by a heat fuse 75. In some embodiments, the proximal portion 71 may include an intermediate layer 68 of braiding while the distal portion 73 does not include an intermediate layer 68. In some embodiments, the length of the distal portion 73 is between about 10 cm and about 30 cm, or between about 15 cm and about 25 cm, or between about 15 cm and about 20 cm. In other embodiments, the proximal portion 71 may include an intermediate layer 68 of braiding, while the distal portion 73 includes an intermediate layer 68 of coil reinforcement. In other embodiments, an intermediate portion (not shown) fused between the proximal portion 71 and the distal portion 73 may be included. The intermediate portion may be of a particular length and at a particular location along the tubular body 64 such that it is configured to span between a vein (e.g., internal jugular vein) and an artery (e.g., common carotid artery), while the distal portion 73 extends substantially into the arterial vasculature and the proximal portion 73 extends substantially into the venous vasculature. For example, in a particular embodiment, about intermediate portion may have a length somewhat similar to the proximal portion 71, while the length of the distal portion 73 is within the ranges described above. In another embodiment, the proximal portion 71, the intermediate portion, and the distal portion 73, each, have a length of about one-third of the total length of the tubular body 64. The intermediate portion would have a flexibility between that of the proximal portion 71 and the distal portion 73.

A radiopaque marker 72 may be coupled to the distal end 60 of the guiding catheter 14 by adhesive or epoxy bonding, swaging, printing, coating, sputtering, ion implantation, or other methods. The radiopaque marker 72 allows for visualization of the distal end 60 of the guiding catheter 14 by x-ray or fluoroscopy, and the radiopaque maker 72 may comprise, platinum, iridium, tantalum, rhenium, tungsten, gold, or an alloy of these materials with each other or with other materials. The distal end 60 of the guiding catheter 14 may have a taper or fillet 74, for example, to aid insertion through a venous wall/arterial wall puncture. The guiding catheter 14 includes a proximal hub 76 having an inner cavity 78 in fluid communication with the lumen 62, and having an optional female luer connector 80 at its proximal end 81. A sideport 82 having a female luer connector 84, a lumen 86 and a stopcock 88 is coupled via an extension tube 90 to the proximal hub 76. The proximal hub 76 includes a valve 92 configured to seal around the shafts of any other component (e.g., the stylet sheath/dilator 16) that is placed through the inner cavity 78 and lumen 62. The valve 92 is also configured to assure that, even without any device placed through the inner cavity 78 or lumen 62, liquid injected through the lumen 86 of the sideport 82 and the extension tube 90 passes through the lumen 62 of the guiding catheter 14, and not out the orifice 94 of the proximal hub 76. In some embodiments, the valve 92 is configured to seal the lumen 62 of the guiding catheter 14 from arterial pressure, such as systolic common carotid pressure, or systolic cerebral artery pressure. In some cases, the user may choose to place a continuous flush on one or both of the female luer connectors 44, 84. For example, a tubing set with heparinize or non-heparinized saline in a pressurized bag (>250 mm Hg). The distal end 60 of the guiding catheter 14 may alternatively have a hydrophilic coating, silicone coating, or other lubricious coating, to aid insertion and/or tracking.

The stylet sheath/dilator 16 comprises a proximal end 120, a distal end 122, and a lumen 124 extending between the proximal end 120 and the distal end 122. The stylet sheath/dilator 16 comprises a tubular body 126 which may be made from a variety of materials, including polymeric materials such as PEBAX® (polyether block amide), Nylon, and polyurethane. The tubular body 126 may include a composite design, such as a lubricious inner layer 128 comprising PTFE, ETFE, or other fluoropolymer, a braided, coil-reinforced, or machined hypo tube intermediate layer 130, and an outer material 132 comprising polymeric materials such as PEBAX® (polyether block amide), Nylon, and polyurethane. The intermediate layer 130 may comprise stainless steel, nickel-titanium alloy, or other metallic material, and may extend from the proximal end 120 to the distal end 122, or from the proximal end 120 to an intermediate location, proximal to the distal end 122. The stylet sheath/dilator 16 may have a continuous outer diameter, or in other embodiments, may taper at the distal end 122, for example, to a smaller diameter. In some embodiments, the lumen 124 of the stylet sheath/dilator 16 has a diameter (or a maximum transverse dimension, if not circular) of between about 0.010 inch and about 0.040 inch, or between about 0.010 inch and about 0.020 inch. In some embodiments, the length of the stylet sheath/dilator 16 between the proximal end 120 and the distal end 122 is between about 95 cm and about 140 cm, or between about 105 cm and about 130 cm.

A radiopaque marker 134 may be coupled to the distal end 122 of the stylet sheath/dilator 16 by adhesive or epoxy bonding, swaging, printing, coating, sputtering, ion implantation, or other methods. The radiopaque marker 134 allows for visualization of the distal end 122 of the stylet sheath/dilator 16 by x-ray or fluoroscopy, and the radiopaque maker 134 may comprise, platinum, iridium, tantalum, rhenium, tungsten, gold, or an alloy of these materials with each other or with other materials. The distal end 122 of the stylet sheath/dilator 16 has a frusto-conical taper and/or fillet 136, for example, to aid insertion through a venous wall and arterial wall puncture. The distal end 122 of the stylet sheath/dilator 16 may alternatively have a hydrophilic coating, silicone coating, or other lubricious coating, to aid insertion and/or tracking. The stylet sheath/dilator 16 includes a proximal hub 138 having a cavity 140 and a flange 142. The stylet sheath/dilator 16 may taper in outer diameter over much or all of its length. For example the diameter at the distal end may be between about 0.020 inch and about 0.032 inch, and taper proximally to between about 0.040 inch and about 0.060 inch.

The stylet 18 comprises a proximal end 144 and a distal end 146. The distal end 146 of the stylet 18 includes a puncture member 151 having one or more cutting surfaces 153 and an extreme distal tip or point 155 (see also FIG. 17). The proximal end 144 of the stylet 18 is attached to a hub 148 having a flange 150. An outer cylindrical surface 152 of the hub 148 is configured to slide freely within the cavity 140 of the proximal hub 138 of the stylet sheath/dilator 16. In some embodiments, a spring 154 (coil or spring washer) is configured to interface with an annular or frusto-conical surface 156 of the hub 148. When the stylet 18 is inserted through the lumen 124 of the stylet sheath/dilator 16, a user may place opposing compressive forces on an end surface 158 of the hub 148 and an annular surface 160 of the flange 142 of the proximal hub 138 to control two-way relative longitudinal movement between the stylet 18 and the stylet sheath/dilator 16. The user may place pressure on the end surface 158 with a thumb while holding the proximal hub 138 between two fingers of the same hand, the two fingers pressing against the annular surface 160 (arrows, FIG. 2). The spring 154 is compressed by the surface 156 as the hub 148 and proximal hub 138 are pressed together. When the hub 148 and proximal hub 138 are released the spring 154 imparts a longitudinal separating force between the hub 148 and the proximal hub 138. In alternative embodiments, a trigger mechanism may be incorporated to force distal longitudinal movement on the stylet 18. In some embodiments, the proximal hub 138 and the hub 148 may be locked together, to freeze their longitudinal position in relation to each other. For example, a friction tab 159 on the hub 148 may be configured to jam against a longitudinally-extending decreased diameter portion 161 within the cavity 140 of the proximal hub 138. The friction tab 159 may be frictionally forced against the decreased diameter portion 161 by a user, by turning (rotating) the proximal hub 138 and hub 148 in opposite directions to each other. The stylet 18 includes a stiff support shaft 162 and a tapered distal section 164 upon which the puncture member 151 is attached. The shaft 162 may comprise stainless steel, nickel titanium alloy, or another relatively had metallic material. The support shaft 162 may have an outer diameter or maximum transverse dimension of between about 0.030 inch and about 0.060 inch, or between about 0.039 inch and about 0.059 inch, or between about 0.045 inch and about 0.055 inch, or between about 0.048 inch and about 0.052 inch.

The puncture member 151 may comprise a trocar-style tip, and may comprise stainless steel or another hard metal. The trocar tip may include three bevels 157 (see FIG. 17), such that the distal tip 155 forms a sharp point, and three cutting surfaces 153 separate the three bevels 157. The three bevels 157 may each be planar, or may each have a concave or convex surface, terminating at a proximal edge 149. The puncture member 151 is configured to penetrate a venous wall and an arterial wall adjacent to the venous wall, thus creating a first opening to allow the system for accessing arterial vasculature from a venous insertion site 10 to access arterial vasculature from a venous insertion (access) site. The puncture member 151 of the stylet 18 may have a maximum transverse dimension of between about 0.010 inch and about 0.028 inch or between about 0.012 inch and about 0.020 inch, or between about 0.014 inch and about 0.018 inch. The puncture member 151 may be radiopaque by having an outer layer (sputtered, ion implanted, etc.) of a radiopaque material such as platinum, iridium, tantalum, rhenium, tungsten, gold, or an alloy of these materials with each other or with other materials. Alternatively, the puncture member 151 may have sufficient radiopacity from its thickness alone. In other embodiments, the puncture member 151 is configured to be echogenic, such that it can be visualized in the vasculature by an external ultrasound probe. For example, a 3.5 MHz probe, a 7.5 MHz probe, or a 10.0 MHz ultrasound probe.

Returning to FIG. 2, an optional clip 37 is illustrated. The clip 37 is configured to be secured to the proximal hub 36 of the curved outer sheath 12 and to be reversably securable to the proximal hub 138 of the stylet sheath/dilator 16 (as shown), or alternatively, to be reversably securable to the proximal hub 76 of the guiding catheter 14. Alternatively, the clip 37 may be attached between the proximal hub 76 of the guiding catheter and the proximal hub 138 of the stylet sheath/dilator 16. The clip 37 comprises a first snap 39 configured to removably snap onto a cylindrical projection 43 of the proximal hub 36 (and/or one of the other proximal hubs), a second snap 45 configured to removably snap onto a cylindrical projection 47 of the proximal hub 138 (and/or one of the other proximal hubs) and a stiff body 49 extending between and rigidly coupled to the first snap 39 and the second snap 45, thus providing a static relationship between the first snap 39 and the second snap 45. Thus, when snapped in place, the clip 37 provides a static relationship between the proximal hub 36 and the proximal hub 138, and thus a static relationship, for example, between the curved outer sheath 12 and the proximal hub of the stylet sheath/dilator 16.

As discussed, the curved portion 32 of the curved outer sheath 12 is configured to have curve retention such that placement of distal portions of the guiding catheter 14, stylet sheath/dilator 16, and stylet 18 within the lumen 25 does not substantially straighten the curved portion 32. Thus, the guiding catheter 14, the stylet sheath/dilator 16, and the stylet 18 may each be configured with a generally straight shape, without their own tip curvature, as shown in FIG. 1. However, it is possible to provide some curvature to one or more of the guiding catheter 14, stylet sheath/dilator 16, and stylet 18. For example, it might be desired that one or more of the guiding catheter 14, stylet sheath/dilator 16, and stylet 18 is capable of tracking through tortuous vasculature, or of flexing or turning to cannulate a particular vessel at a bifurcation, or avoid a blocked area. In some embodiments, one of more of the guiding catheter 14, stylet sheath/dilator 16, and stylet 18 may have distal sections that either are supplied with particular curve shapes, or that are custom shapeable (e.g., by a physician using steam, prior to a procedure).

Figure 3:
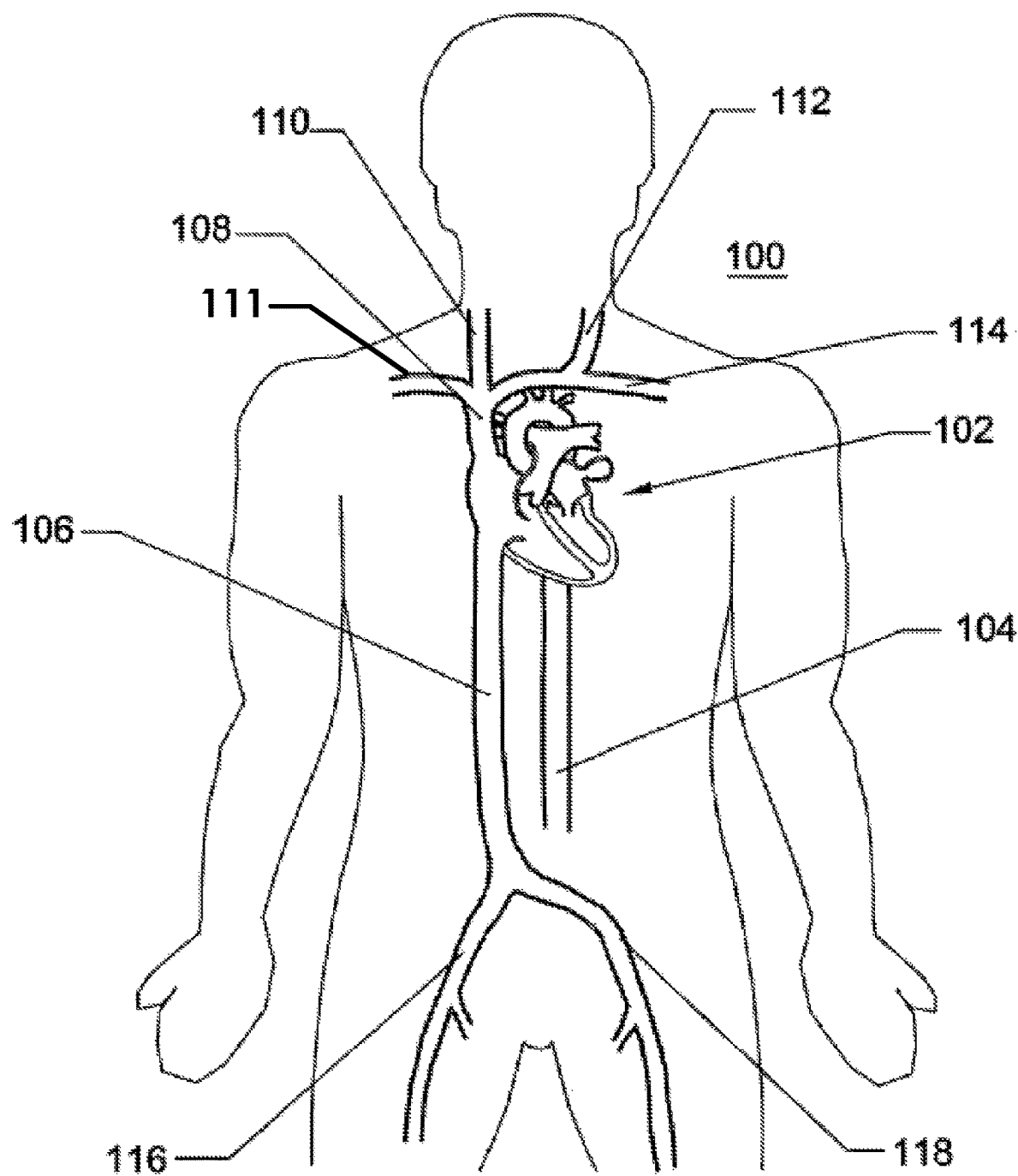
FIG. 3 is a front view representation of the human venous circulatory system including the heart and the great veins.

FIG. 3 is a schematic frontal (anterior) illustration (looking posteriorly) of a human patient 100 comprising a heart 102, a descending aorta 104, an inferior vena cava 106, a superior vena cava 108, a right jugular vein 110, a left jugular vein 112, a right subclavian vein 111, a left subclavian vein 114, a right femoral vein 116 and a left femoral vein 118. In this illustration, the left anatomical side of the body of the patient 100 is toward the right of the illustration.

Figure 4:
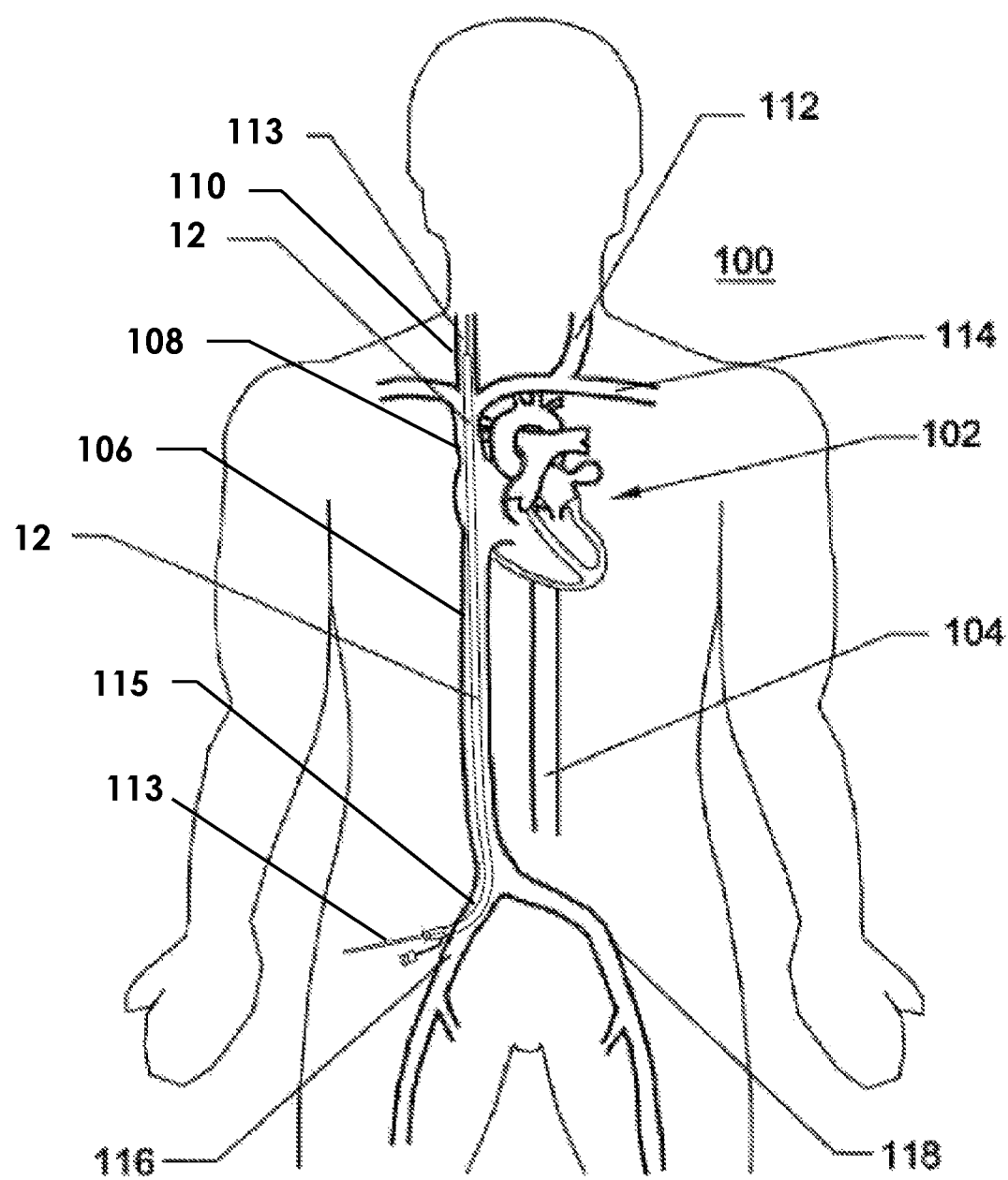
FIG. 4 is a front view representation of the human venous circulatory system with an access sheath inserted.
Figure 5:
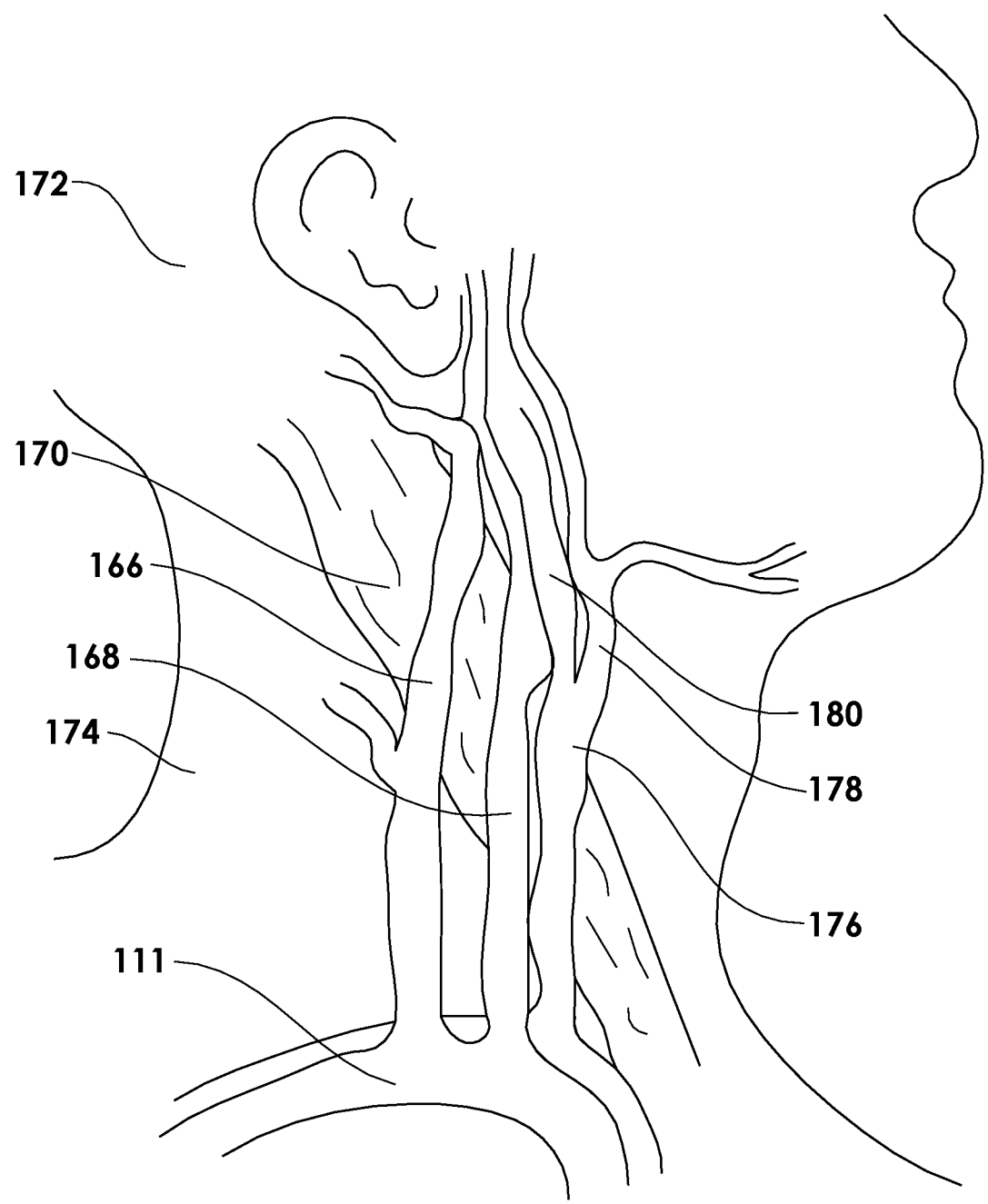
FIG. 5 is a side view representation of veins and arteries in the human neck area.
Figure 6:
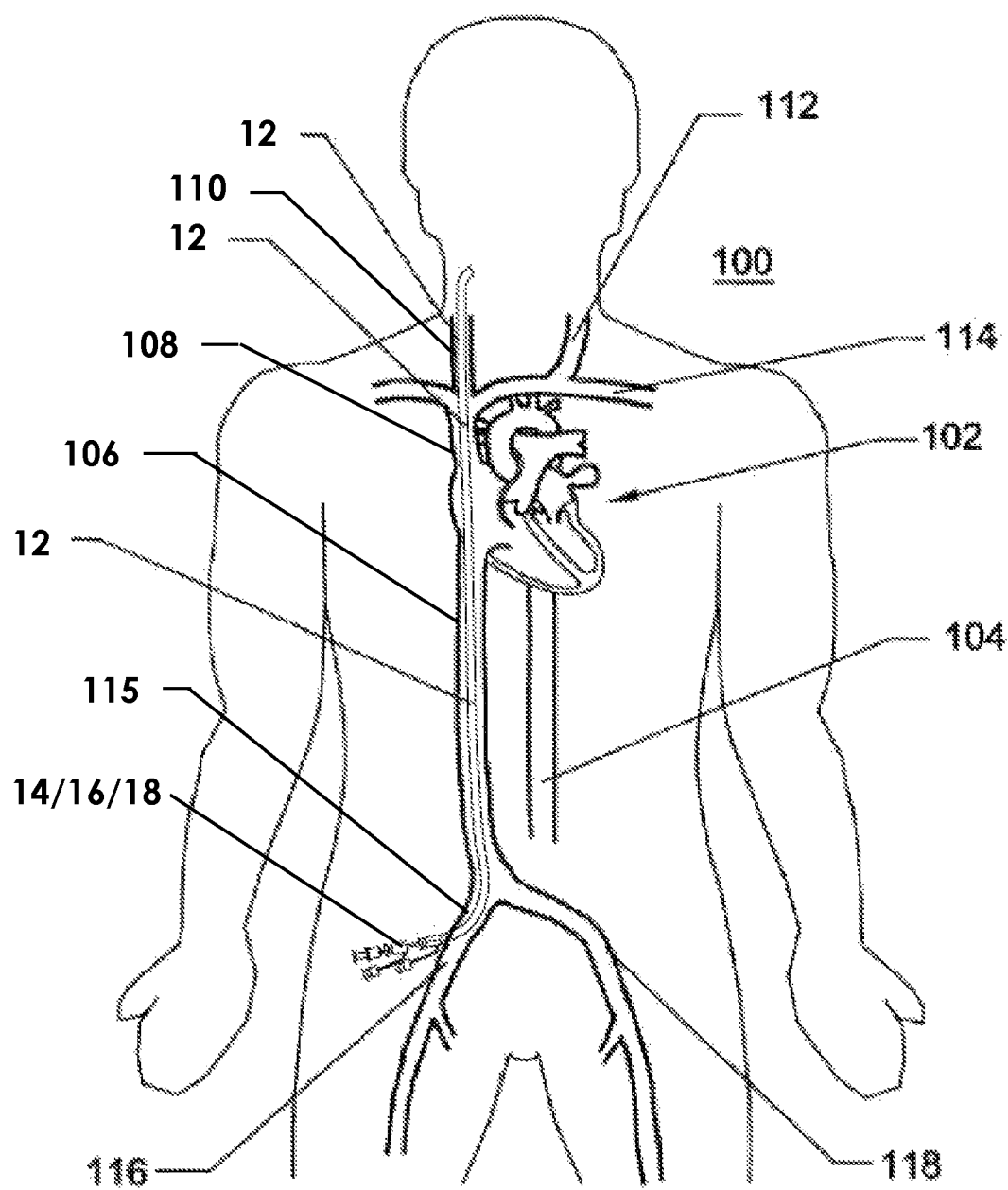
FIG. 6 is a front view representation of the human venous circulatory system with the system for accessing arterial vasculature from a venous insertion site of FIG. 1 inserted.

Turning to FIG. 4, a femoral vein (right femoral vein 116) is punctured with a hypodermic needle (not shown), using the Seldinger technique at puncture site 115, and a guidewire 113 is placed into the venous system. The needle is removed and the curved outer sheath 12 is placed over the guidewire 113. In FIG. 4, the curved outer sheath 12 is extended through the inferior vena cava 106, the superior vena cava 108, and the right jugular vein 110. More detail of the jugular veins 110, 112 is shown in FIG. 5, with the sternocleidomastoid muscle 170, the head 172, and neck 174 shown for reference purposes. The right external jugular vein 166 and right internal jugular vein 168 branch from the right subclavian vein 111. The proximity and alignment of the right internal jugular vein 168 and the right common carotid artery 176 can be clearly seen in FIG. 5. A similar proximity and alignment is commonly present with the left internal jugular vein and the left common carotid artery. The right common carotid artery 176 branches into the right external carotid artery 178 and the right internal carotid artery 180. It is the intention of this disclosure to provide systems and methods for providing access to the internal carotid artery and cerebral arteries from a venous access (external puncture) site via an internally-made transvascular puncture between an internal jugular vein and a common carotid artery. Turning to FIG. 6, a guiding catheter 14, stylet sheath/dilator 16, and stylet 18 are placed into the curved outer sheath 12 that has been placed into the venous system, such that the system for accessing arterial vasculature from a venous insertion site 10 can be placed in the internal jugular vein adjacent the common carotid artery.

Figure 7:
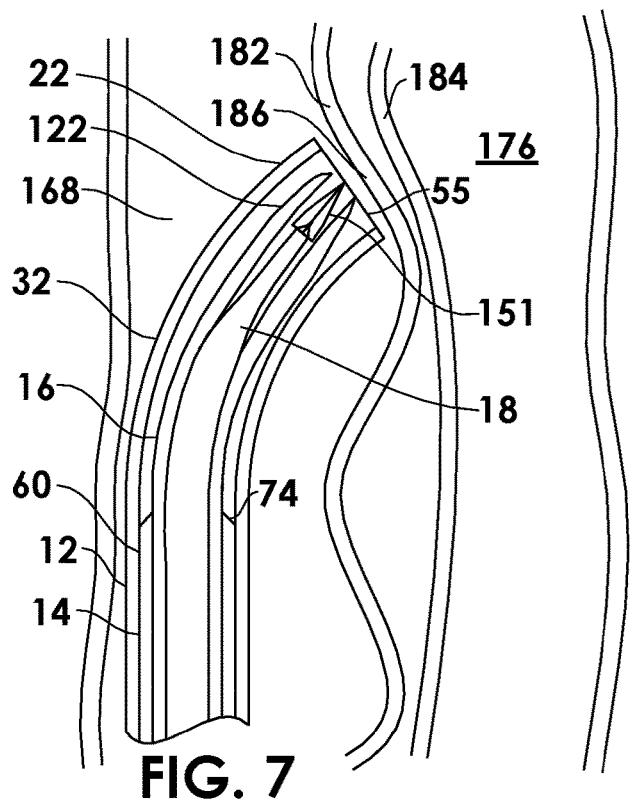
FIG. 7 is a sectional view of the system for accessing arterial vasculature from a venous insertion site in a first position.

FIGS. 7-16 illustrate the functional elements of the system for accessing arterial vasculature from a venous insertion site 10 used in the method of accessing the arterial vasculature from a venous starting point. In use, the system for accessing arterial vasculature from a venous insertion site 10 is placed such that it extends from the puncture site 115 at the femoral vein (FIG. 6) with the distal end 22 of the curved outer sheath 12 within the right internal jugular vein 168, and directly adjacent the right common carotid artery 176. The venous wall 182 of the right internal jugular vein 168 is in proximity to the arterial wall 184 of the right common carotid artery 176, and it is one objective of the system for accessing arterial vasculature from a venous insertion site 10 to perform the puncture of both walls 182, 184 at the same time. The puncture member 151 of the stylet 18 is configured to puncture both the venous wall 182 and the 184 in a single motion, creating an initial opening between vein and artery. The curved portion 32 of the curved outer sheath 12 is positioned as shown in FIG. 7 with the distal end 22 and distal orifice 55 of the curved outer sheath 12 against the venous wall 182 (or otherwise in close proximity thereto). It may be desired to have the distal end 22 snug or somewhat tight (e.g., with a normal force) against the venous wall 182. A site 186 on the venous wall 182 is chosen in which the venous wall 182 is sufficiently close to the arterial wall 184. Fluoroscopy or radiography may be used to identify the chosen site 186. In some cases, dilute or undilute contrast media may be injected into the right internal jugular vein 168 and/or the right common carotid artery 176, using one or more separate catheters, or using the lumen 25 of the curved outer sheath 12, the lumen 62 of the guiding catheter 14, or even the lumen 124 of the stylet sheath/dilator 16. The proximal hub 138 of the stylet sheath/dilator 16 may optionally include a luer connector to facilitate contrast injection. In the position shown in FIG. 7, the guiding catheter 14 is slightly retracted from the distal end 22 of the curved outer sheath 12, while the distal end 122 of the stylet sheath/dilator 16 and the puncture member 151 of the stylet 18 are located at or located close to the distal end 22 of the curved outer sheath 12. However, the position of the guiding catheter 14 can alternatively be further retracted (position in FIG. 9), or can be further extended, so that the distal end 60 of the guiding catheter 14 is at or close to the distal end 22 of the curved outer sheath 12. The guiding catheter 14 may even be extended or retracted to a particular point within the lumen 25 of the curved outer sheath 12 in order to control the amount of back up strength on the curved portion 32 of the curved outer sheath 12.

Figure 8:
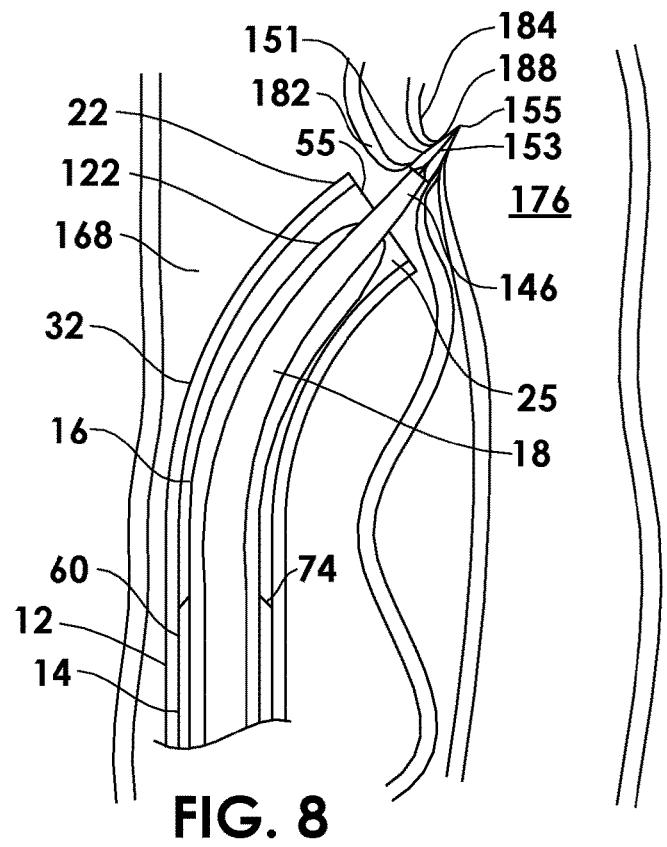
FIG. 8 is a sectional view of the system for accessing arterial vasculature from a venous insertion site in a second position.
Figure 9:
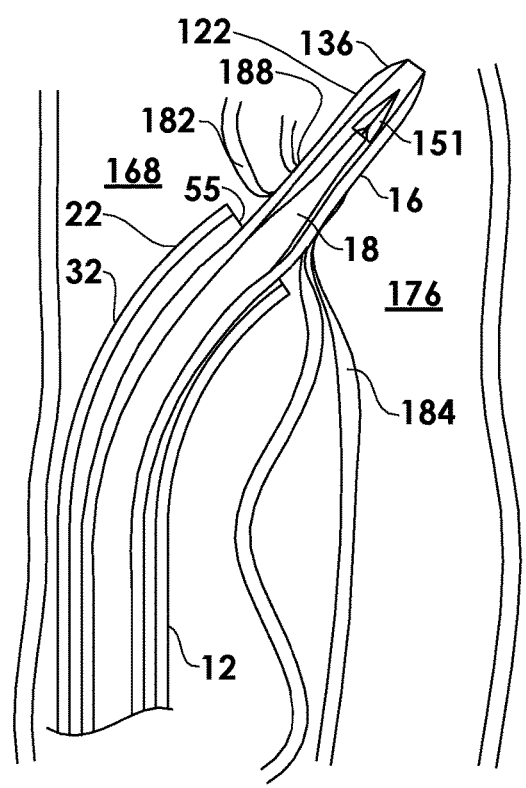
FIG. 9 is a sectional view of the system for accessing arterial vasculature from a venous insertion site in a third position.
Figure 10:
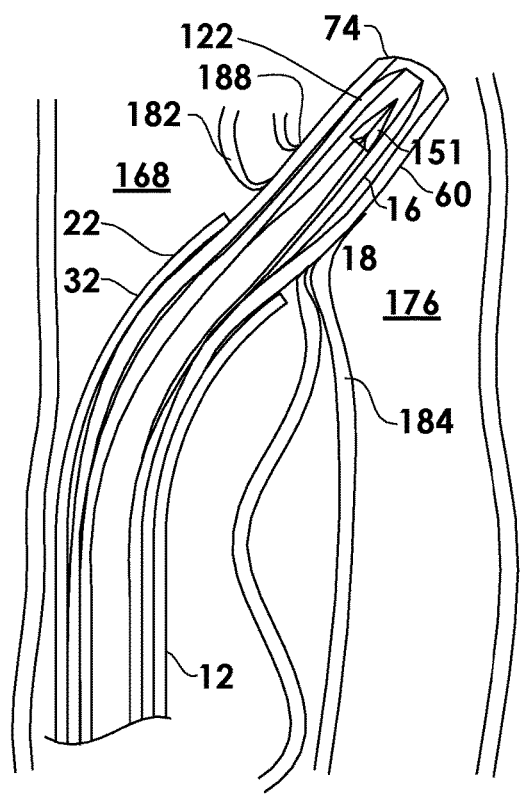
FIG. 10 is a sectional view of the system for accessing arterial vasculature from a venous insertion site in a fourth position.
Figure 11:
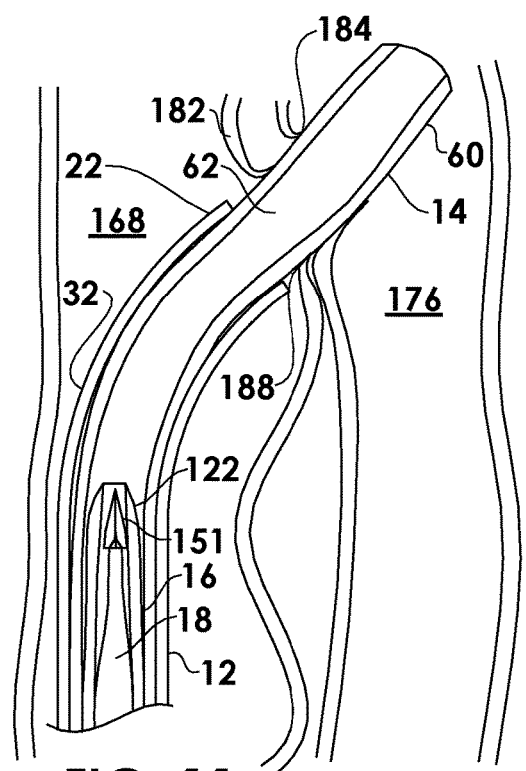
FIG. 11 is a sectional view of the system for accessing arterial vasculature from a venous insertion site in a fifth position.

Turning to FIG. 8, the user pushes the proximal hub 138 and the hub 148 together (arrows, FIG. 2), while stabilizing the proximal hub 138 either manually, or with the clip 37, to force the puncture member 151 through the venous wall 182 and arterial wall 184. The clip 37 (FIG. 2) may be used, such that the longitudinal movement of the stylet 18 is directly relative to one or more of the curved outer sheath 12, the guiding catheter 14, or the stylet sheath/dilator 18. Thus, the curved outer sheath 12, the guiding catheter 14, and/or the stylet sheath/dilator 18 may be held static while the puncture member 151 is forced through the venous wall 182 and arterial wall 184. For example, the distal tip 22 of the curved outer sheath 12 may be held in its position opposite the venous wall 182 while the puncture member 151 is forced through the venous wall 182 and the arterial wall 184. The user may choose to visualize the position of the puncture member 151 of the stylet 18 using an external ultrasound probe (e.g., against the neck 174) in the case of an echogenic puncture member 151, or may alternatively, or optionally, use fluoroscopy. Alternatively, the radiopaque marker 134 of the stylet sheath/dilator 16 may be echogenic, such that the external ultrasound probe may visualize its location. Other echogenic components may be coupled to the stylet sheath/dilator 16. In FIG. 8, the distal tip 155 begins the puncture and the cutting surface 153 allows the entire puncture member 151 to cut through the venous wall 182 and arterial wall 184, creating an opening 188. The user then pushes the entire puncture member 151 past the opening 188 so that at least the distal end 146 of the stylet 18 traverses the opening 188. The system for accessing arterial vasculature from a venous insertion site 10 may be configured such that the distal tip 155 of the puncture member 151 is able to extend no more than 8 mm past the distal end of the stylet sheath/dilator, or no more than 5 mm, or no more than 3 mm. As shown in FIG. 9, the user then passes the distal end 122 of the stylet sheath/dilator 16 over the stylet 18 to further dilate the opening 188 in the venous wall 182 and arterial wall 184. The taper 136 of the stylet sheath/dilator 16 aids dilation of the opening 188 and the insertion of the stylet sheath/dilator 16 through the opening 188. The taper 136 may have a smooth surface, so that no tearing of the venous wall 182 or arterial wall 184 occurs as the distal end 122 of the stylet sheath/dilator 16 is being passed through and dilates the opening 188. The user now advances the guiding catheter 14 within the curved outer sheath 12 by grasping the proximal hub 76 and moving it distally (toward the proximal hub 36 of the curved outer sheath 12) (see FIG. 2). The user then further extends the distal end 60 of the guiding catheter 14 out of the lumen 25 of the curved outer sheath 12, as shown in FIG. 10. The taper 74 of the guiding catheter 14 aids the further dilation of the opening 188 and thus, the passage of the guiding catheter further through the opening 188 and further into the right common carotid artery 176. It should be noted that, although radiopaque markers 34, 72, 134 are shown in FIG. 1, an alternative is to make the tubular bodies 24, 64, 126 themselves radiopaque, at at least at their distal portions. For example, the polymeric materials may be doped with radiopaque material, such as barium sulfate ($BaSO_4$), bismuth subcarbonate ($Bi_2O_2CO_3$), bismuth oxychloride (BiOCl), bismuth trioxide ($Bi_2O_3$), Tungsten (W), or titanium dioxide ($TiO_2$). Alternatively, the stylet 18 may be removed from the lumen 124 of the stylet sheath/dilator 16 and replaced by a guidewire (e.g., 0.014 inch to 0.021 inch, or 0.016 inch to 0.018 inch) (not shown), to add stability when the guiding catheter 14 is passed over the stylet sheath/dilator 16.

Figure 12:
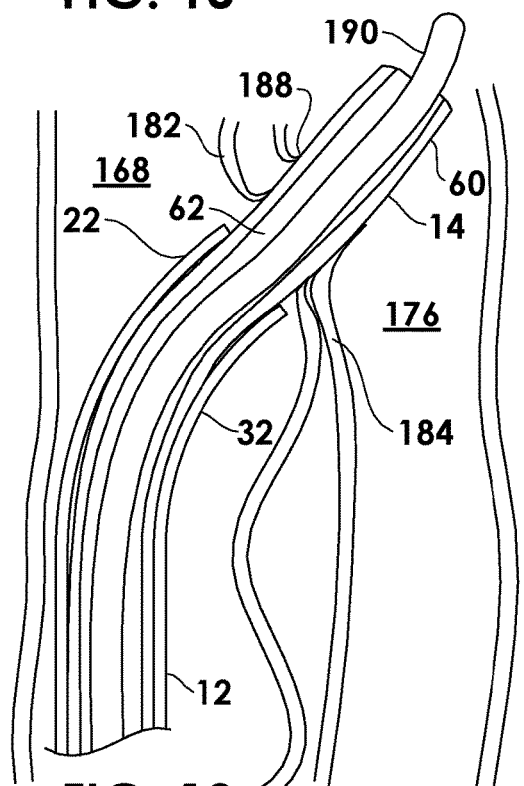
FIG. 12 is a sectional view of the system for accessing arterial vasculature from a venous insertion site in a sixth position.
Figure 13:
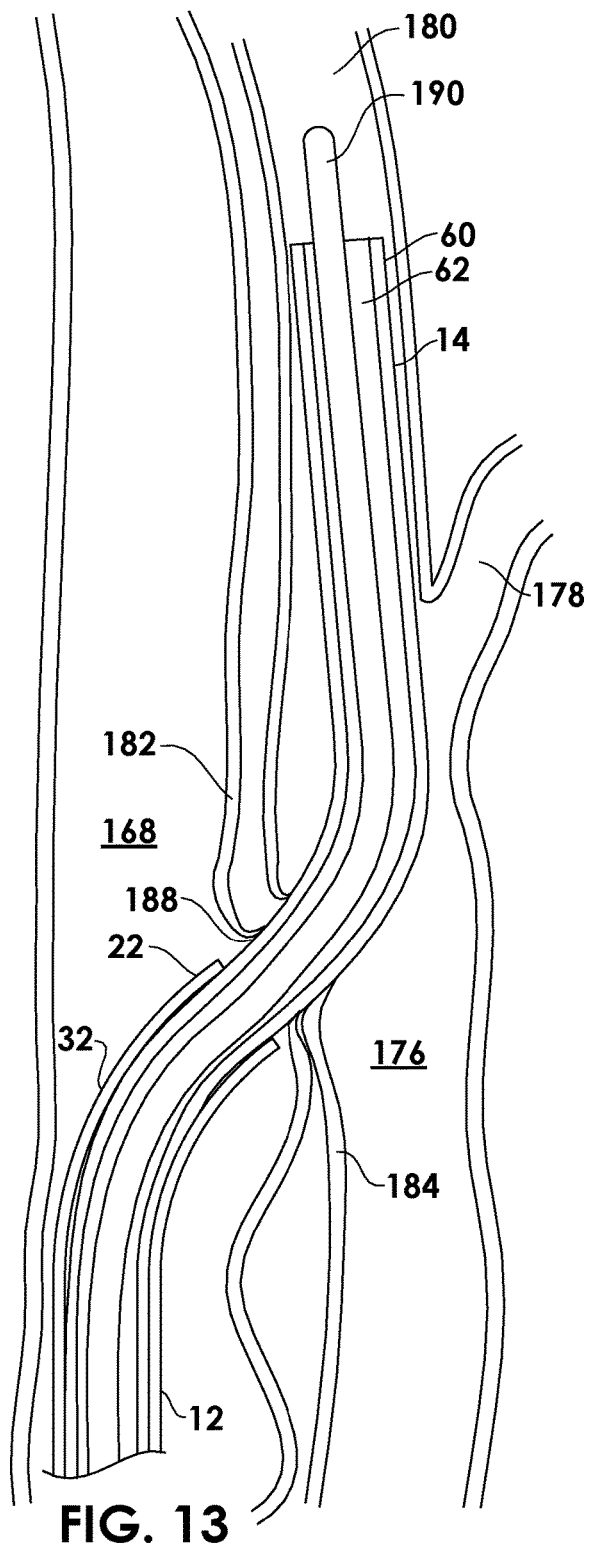
FIG. 13 is a sectional view of the system for accessing arterial vasculature from a venous insertion site in a seventh position.
Figure 14:
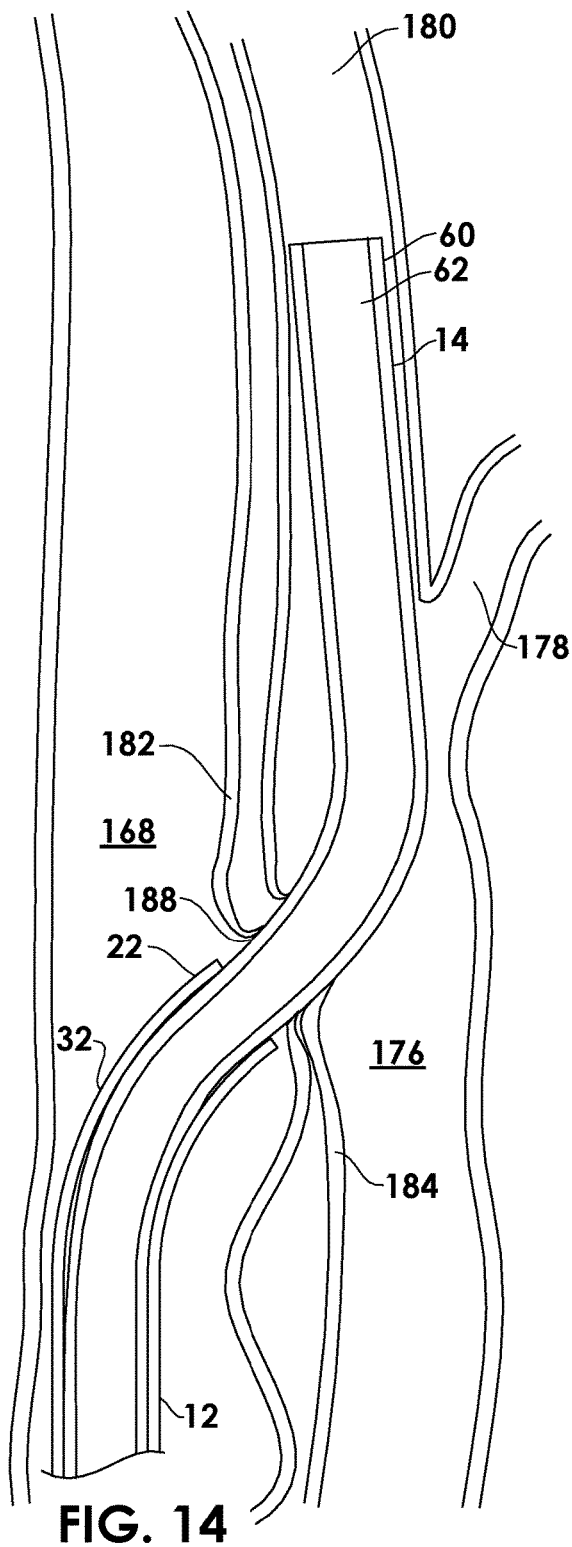
FIG. 14 is a sectional view of the system for accessing arterial vasculature from a venous insertion site in an eighth position.

The user may track the guiding catheter 14 further distal in the right common carotid artery 176, or into the right internal carotid artery 180 (FIG. 5) with the stylet sheath/dilator 16 and the stylet 18 still advanced, as shown in FIG. 10. Alternatively, the stylet sheath/dilator 16 may be removed completely from the guiding catheter 14, while the guiding catheter 14 extends through the curved outer sheath 12 (FIG. 11), and a guidewire 190 may be inserted through the lumen 62 of the guiding catheter 14, and into the right common carotid artery 176 (and/or the right internal carotid artery 180) (FIG. 12). The guidewire 190 may be the same as the guidewire 113 shown in FIG. 4, or may be a different guidewire (different length, different flexibility, different diameter). In some cases, a 0.035 inch hydrophilically-coated guidewire may be used as the guidewire 190, in order to track the guiding catheter 14 to a more distal location, such as the right internal carotid artery 180 (FIG. 13). When the guiding catheter 14 is in a desired position for backup support, contrast delivery, and arterial subselection, the user removes the guidewire 190 (FIG. 14).

Figure 15:
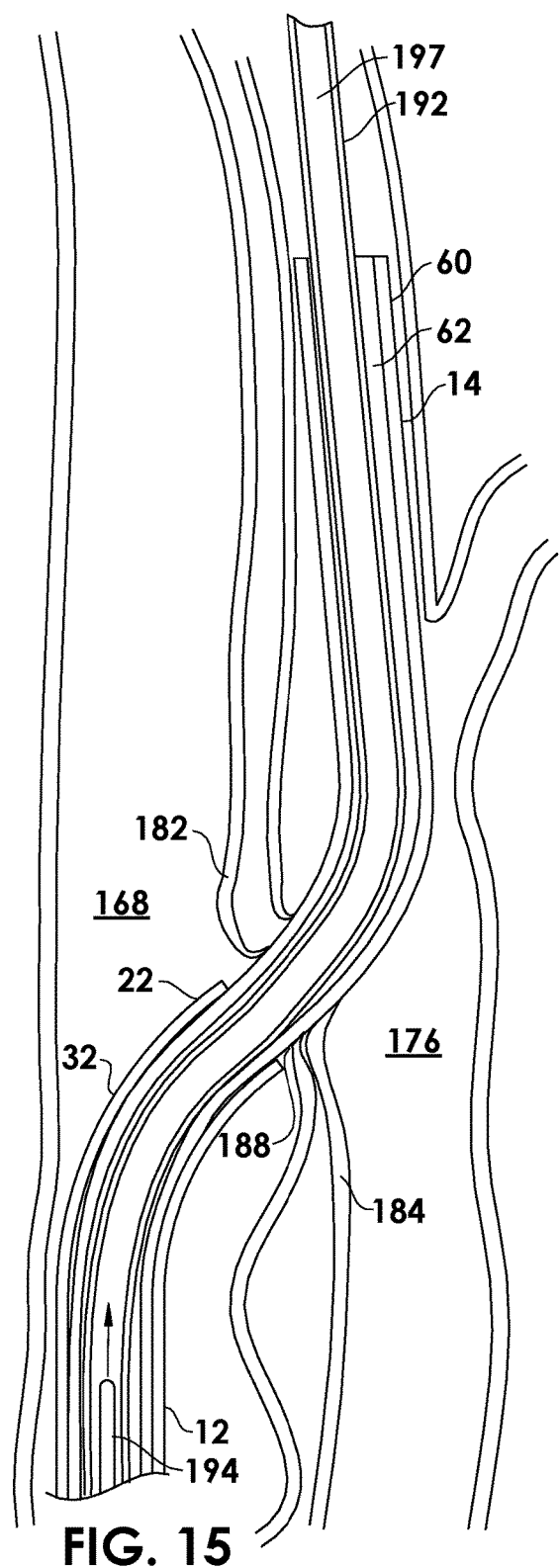
FIG. 15 is a sectional view of the system for accessing arterial vasculature from a venous insertion site in a ninth position.
Figure 16:
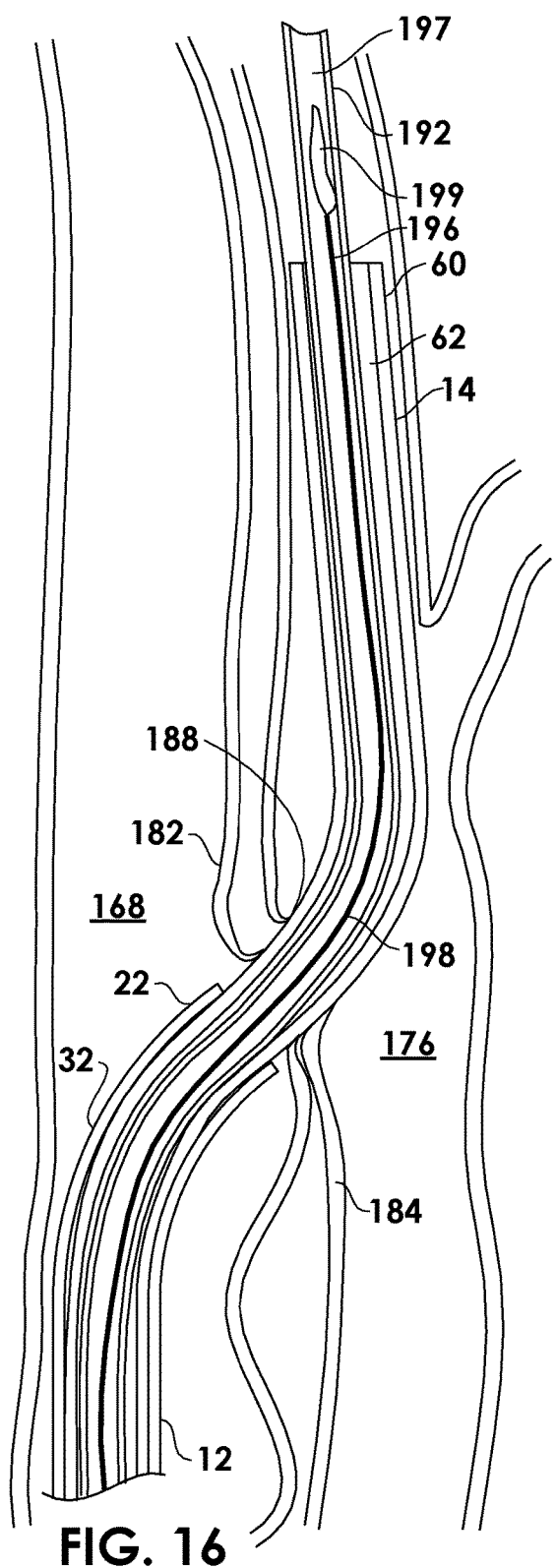
FIG. 16 is a sectional view of the system for accessing arterial vasculature from a venous insertion site in a tenth position.

Turning to FIG. 15, to perform an endovascular procedure in the cerebral circulation, the user inserts a microcatheter 192 into the inner cavity 78 of the proximal hub 76 of the guiding catheter 14, advances the microcatheter 192 through the lumen 62 of the guiding catheter 14, and out of the distal end 60 of the guiding catheter 14. The microcatheter 192 can then be tracked to a desired target site for performing the therapeutic or diagnostic procedure of choice. A microguidewire 194 can be used within the lumen 197 of the microcatheter 192, to further aid in the distal tracking of the microcatheter 192. Alternatively, a flow-directed catheter can be used instead of the microcatheter 192. Flow-directed catheters are configured to be distally-deliverable without the use of microguidewires. Drugs, saline, or contrast agents may be delivered down the lumen 197 of the microcatheter 192 (or of the flow-directed catheter) to perform a therapeutic or diagnostic action. As shown in FIG. 16, an interventional device 196 comprising a proximal shaft 198 and a deliverable element 199 may be delivered down the lumen 197 of the microcatheter 192 to the target site. The deliverable element 199 may comprise a detachable or releasable embolic device (coil, braided ball, polymeric filler material), or an energy-delivery element (radiofrequency, ultrasound), or a stent. When the procedure is completed, further fluoroscopy may be performed to determine the status of the procedure, and then the shaft 198 may be removed from the microcatheter 192, the microcatheter 192 may be removed from the guiding catheter 14, the guiding catheter 14 may be removed from the curved outer sheath 12, and the curved outer sheath 12 may be removed from the puncture site 115. Closure of the venous puncture site 115 can be done faster, more reliably, and with more safety than typical closures of arterial puncture sites (femoral artery, etc.) The significantly lower venous pressure allows easier compression, and less flow-related shear stress. The venous vessel wall is also more compressible than stronger arterial walls.

The opening 188 will often close spontaneously if it has a dilated diameter of a particular French size or less, depending upon the particular shear stress, disease state, coagulation characteristics, or other characteristics in the particular site and of the particular patient. In some cases, if a larger dilated diameter is created (purposefully or not), a closure device may be used to adjunctively close the opening 188 completely, or partially (so that it can then be lessened in size to allow it to close spontaneously). Closure devices may be used such as those described in U.S. Pat. No. 9,445,799, issued Sep. 20, 2016, and titled "Multi-layer braided structures for occluding vascular defects," which is hereby incorporated by reference in its entirety for all purposes.

Although the right side of the patients venous and arterial system is presented, alternatively, the left side may be used. In some cases, both the right side and the left side may be used, for example if multiple catheters are to be delivered to the cerebral vasculature. In addition, the venous plexus around the vertebral arteries may alternatively used as a venous-to-arterial crossing site. Alternatively, or additionally, instead of a puncture site 115 at the femoral vein, other puncture sites may be utilized, including, but not limited to, a brachial vein, an axillary vein, or a subclavian vein.

By providing a system to easily allow a user to bypass tortuous or diseased anatomy (e.g., arterial vasculature), procedure times can be significantly reduced, complication rates can be reduced, because of fewer bleeding complications or fewer distal emboli, including thromboemboli that can result in stroke, or from better control of the intracranial devices themselves. The better control results from freer movement because of less resistance from, for example, diseased peripheral arteries. Thus, more precise and stable delivery of devices is possible. Procedure time is also decreased, because each step is fraught with fewer complications or interruptions. The time to reach the target site is also reduced, which is particularly important in an emergent procedure, such as a ruptured aneurysm, or a thromboembolic stroke.

The combination of the curved outer sheath 12, a guiding catheter 14, and stylet sheath/dilator 16, and a stylet 18 into a single system 10, allows a single user to access the carotid arteries and their direct and indirect branch vessels via a venous puncture site 115. The coupling of the proximal hubs 36, 76, 138, 148 (via the friction tab 159/decreased diameter portion 161 and/or the clip 37), and the spring 154 between the proximal hub 138 and the hub 148 which allows for the end surface 158/annular surface 160 action, further facilitate single user performance.

An alternative stylet 218 and stylet sheath/dilator 216 are illustrated in FIG. 18. The stylet sheath/dilator 216 comprises a proximal end 220, a distal end 222. A lumen 224 extends between the a distal tip 225 and an orifice 223 that is located proximal to the distal tip 225 and distal to the proximal end 220. The distal end 222 of the stylet sheath/dilator 216 comprises a tubular body 226 which may be made from a variety of materials, including polymeric materials such as PEBAX® (polyether block amide), Nylon, and polyurethane. The tubular body 226 may include a composite design, such as a lubricious inner layer 228 (FIG. 19) comprising PTFE, ETFE, or other fluoropolymer, a braided, coil-reinforced, or machined hypo tube intermediate layer 230, and an outer material 232 comprising polymeric materials such as PEBAX® (polyether block amide), Nylon, and polyurethane. The intermediate layer 230 may comprise stainless steel, nickel-titanium alloy, or other metallic material. The tubular body 226 may have a continuous outer diameter, or in other embodiments, may include a taper 236 at the distal end 222. The length of the tubular body 226, and thus, as illustrated in the embodiment of FIGS. 18-20, the length between the distal tip 225 of the distal end 222 and the longitudinal location of the orifice 223, may be between about 0.25 cm and about 30 cm, or between about 2 cm and about 25 cm, or between about 15 cm and about 30 cm, or between about 5 cm and about 10 cm. In some embodiments, the lumen 224 of the stylet sheath/dilator 216 has a diameter (or a maximum transverse dimension, if not circular) of between about 0.010 inch and about 0.040 inch, or between about 0.010 inch and about 0.020 inch. An elongate support shaft 227 has a distal end 229 having a tapering diameter or transverse dimension, which is connected to the tubular body 226 at its proximal end 231. The elongate support shaft 227 may comprise a solid metallic material, such as stainless steel or nickel-titanium alloy, and may also include a lubricious covering, such as silicone or a hydrophilic coating. In some embodiments, the total length of the stylet sheath/dilator 216 between the proximal end 220 and the distal tip 225 is between about 95 cm and about 140 cm, or between about 105 cm and about 130 cm. The elongate support shaft 227, by virtue of comprising a solid metal material, has a high tensile strength, even with a relatively small outer diameter or transverse dimension. Thus, the proximal portion 233 of the stylet sheath/dilator 216 has a low profile, and is configured to extend in tandem (next to) with the stylet 218. Only at their distal portions is the stylet 218 configured to extend through the lumen 224 of the tubular body 226 of the stylet sheath/dilator 216.

A radiopaque marker 234 may be coupled to the distal end 222 of the stylet sheath/dilator 216 by adhesive or epoxy bonding, swaging, printing, coating, sputtering, ion implantation, or other methods. The radiopaque marker 234 allows for visualization of the distal end 222 of the stylet sheath/dilator 216 by x-ray or fluoroscopy, or even, when configured to be echogenic, by an externally-applied ultrasound probe. The radiopaque maker 234 may comprise, platinum, iridium, tantalum, rhenium, tungsten, gold, or an alloy of these materials with each other or with other materials. The tubular body 226 may additionally have another radiopaque marker located at the orifice 223 for further visualization. The distal end 222 of the stylet sheath/dilator 216 has a frusto-conical taper and/or fillet 236, for example, to aid insertion through a venous wall and arterial wall puncture. The distal end 222 of the stylet sheath/dilator 216 may alternatively have a hydrophilic coating, silicone coating, or other lubricious coating, to aid insertion and/or tracking. The proximal end 220 of the stylet sheath/dilator 216 is attached to a proximal hub 238 having a flange 239 and a translating member 242 having a cavity 240 configured for clipping/snapping a shaft. The translating member 242 is longitudinally slidable along the proximal hub 238 within a groove 241. A user may apply a distally-directed force (arrow) onto a proximal ledge 245 of the translating member 242, which longitudinally moves the translating member 242 distally, and compresses a compression spring 243. Upon releasing the force, the compression spring 243, via its restoring biasing force, causes the translating member 242 to return proximally to its original position.

The stylet 218 comprises a proximal end 244 and a distal end 246. The distal end 246 of the stylet 218 includes a puncture member 251 having a cutting surface 253 and a distal tip 255. The proximal end 244 of the stylet 218 is attached to a hub 248 having a contact surface 250. A support shaft 262 of the stylet 218 may have an outer diameter or maximum transverse dimension of between about 0.030 inch and about 0.070 inch, or between about 0.045 inch and about 0.055 inch, or between about 0.048 inch and about 0.052 inch, tapering distally to a smaller diameter at a tapered distal section 264. Because the majority of the length of the support shaft 262 (not including the tapered distal section 264) of the stylet 218 does not have to fit through the lumen 224 of the tubular body 226, and because the support shaft 227 of the stylet sheath/dilator 216 is made with a lower profile, the diameter of the support shaft 262 may be made larger, thus supplying a large amount of pushability, to drive the puncture member 251 through venous and arterial walls. The support shaft 227 and the increased-diameter support shaft 262 are still able to fit adjacent each other within the lumen 62 of the guiding catheter 14.

Turning to FIGS. 19-20, in some embodiments, the maximum diameter $D_1$ of the puncture member 251 is larger than the distal tip diameter $D_2$ of the lumen 224 of the tubular body 226 of the stylet sheath/dilator 216. The stylet sheath/dilator 216 and the stylet 218 can be assembled together in relatively slideable connection by first, prior to assembling the puncture member 251 onto the tapered distal section 264 of the support shaft 262, by placing a stop ring 259 over the tapered distal section 264 and securing it in place. For example, if the ring comprises a metal, it may be soldered, swaged, crimped, brazed, welded, or adhesively or epoxy bonded. Then, the tapered distal section 264 of the support shaft 262 of the stylet 218 is inserted into the lumen 224 of the tubular body 226 of the stylet sheath/dilator 216, again, before the puncture member is assembled onto the stylet 218. The tapered distal section 264 is inserted into the orifice 223 and extended distally. With the tapered distal section 264 partially extending distally from the lumen 224 (FIG. 20), the puncture member 251 is then secured to the distal end 257 of the tapered distal section 264. The longitudinal positioning between the stylet 218 and the stylet sheath/dilator 216 has two longitudinal extreme positions. In FIG. 19, the proximal edge 249 of the puncture member 251 abuts the distal tip 225 of the tubular body 226 of the stylet sheath/dilator 216. In FIG. 20, the distal edge 261 of the stop ring 259 abuts the proximal end 231 of the tubular body 226 of the stylet sheath/dilator 216. Returning to FIG. 18, the support shaft 262 of the stylet 218 is clipped into the cavity 240 while the stylet 218 and stylet sheath/dilator 216 are in the position shown in FIG. 19. Thus, to articulate the puncture member 251 (e.g., through a venous wall and arterial wall) a user places a distally-directed longitudinal force (e.g., by the user's thumb) on the contact surface 250 of the hub 248 (while pressing in an opposite direction against the flange 239, for example) to move the puncture member 251 to the position shown in FIG. 20, while also causing the compression spring 243 to be compressed. When the user releases pressure, the compression spring 243 causes the puncture member 251 to return to the position shown in FIG. 19. In the configuration of FIG. 19, the outer contours of the puncture member 251 and the taper/fillet 236 of the tubular body 226 of the stylet sheath/dilator 216 form a composite tapered tip 217. The tubular body 226 of the stylet sheath/dilator 216 can thus be more easily advanced through a puncture made by the puncture member 251 when the composite tapered tip 217 elements are moved in unison.

Alternatively, the diameter of the support shaft 262 can be configured such that its maximum diameter or maximum transverse dimension is less than the minimum dimension of the lumen 224 of the tubular body 226 of the stylet sheath/dilator 216. In addition, the hub 248 of the stylet 218 may be made to be attachable and detachable from the support shaft 262. Thus, by removing the hub 248 from the stylet 218, the stylet sheath/dilator 216 becomes a single-operator exchange device, such that it may be removable by a single operator who is holding the stylet 218 with one hand and the stylet sheath/dilator 216 with the other hand. The stylet sheath/dilator 216 can then be easily replaced by another stylet sheath/dilator 216, while maintaining the stylet 218 in its post-puncture position, with the puncture member 251 across the punctured venous wall and arterial wall, and the support shaft 262 extending proximally. Additionally, another type of single-operator exchange catheter may be inserted over the support shaft, while maintaining the stylet 218 in its post-puncture position, with the puncture member 251 across the punctured venous wall and arterial wall.

Figure 21:
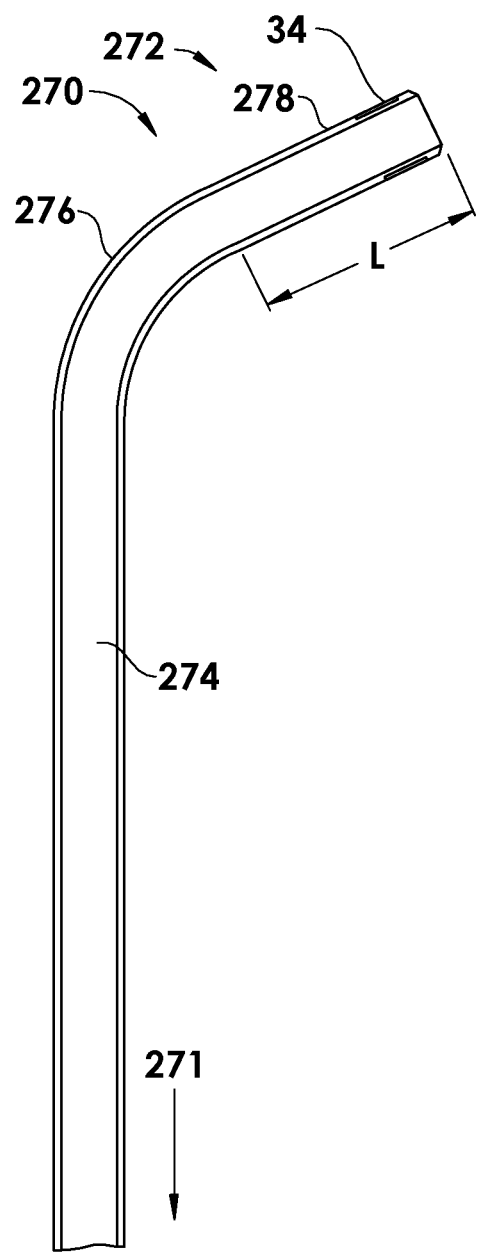
FIG. 21 is a partial sectional view of the distal end of an alternative curved outer sheath according to an embodiment of the present disclosure.

FIG. 21 illustrates an alternative curved outer sheath 270 for use with the system for accessing arterial vasculature from a venous insertion site 10, in some cases, in place of the curved outer sheath 12. The curved outer sheath 270 comprises a proximal end 271, a distal end 272, and a lumen 274 extending between the proximal end 271 and the distal end 272. The materials, sizes, and uses described in relation to the curved outer sheath 12 can be used with the curved outer sheath 270. At the distal end 272 of the curved outer sheath 270 is a curved portion 276 which is configured to provide targeted entry of the stylet 18 through an arterial wall and an adjacent venous wall, much in the same manner as that described in relation to the curved outer sheath 12. The curved portion 276 may include the same curve radius of curvature characteristics arc sweep characteristics, and curve retention characteristics as those described in relation to the curved outer sheath 12. However, located distally to the curved portion 276 is a straight portion 278 having a length L. In some patients, the straight portion 278 is helpful for guiding the stylet 18 through the venous wall and the arterial wall, and/or is helpful a providing the appropriate pressure against the venous wall. In some embodiments, the length L of the straight portion 278 is between about 0.25 cm and about 5.00 cm, or between about 0.50 cm and about 3.00 cm. In some embodiments, the length L can be configured to be the same or longer than the total length of the tubular body 226 of the stylet sheath/dilator 216 presented in the embodiment of FIGS. 18-20. In those embodiments, it may be desirable to provide a relatively stiff tubular body 226 that is completely contained within the straight portion 278, and thus is maintained in a straight condition when the puncture is performed. Thus, friction between the tapered distal section 264 of the stylet 218 and the inner layer 228 of the tubular body 226 of the stylet sheath/dilator 216 is minimized because of reduced internal normal forces. The reduction in friction further aids the support shaft 262 in controllably forcing the puncture member 251 through the venous wall and arterial wall, when so manipulated by a user.

FIG. 22 illustrates a guiding catheter 300 having a distal end 302, a proximal end 303, a first lumen 304 extending between the distal end 302 and the proximal end, and a second lumen 306 extending between the distal end 302 and an exit orifice 308. The second lumen 306 joins with the first lumen 304 internally at a bifurcation 310. The exit orifice 308 includes a seal 312, configured to seal around a shaft that is passed through the second lumen 306, such as the shaft of a guidewire or catheter. The seal 312 may be configured to also seal when no shaft pass through it, as in FIG. 22. The seal 312 may be configured to seal at least systolic venous blood pressure. In some embodiments, the seal 312 may be configured to seal at least systolic arterial blood pressure. In some embodiments, the seal 312 is configured to seal at a pressure of at least about 200 mm Hg, or at least about 250 mm Hg, or at least about 300 mm Hg. The seal 312 may comprise a diaphragm, a duck-bill, or a reduced-diameter portion. The guiding catheter 300 has an outer surface 314, and may comprise the same materials, lengths, diameters, and constructions described herein for the guiding catheter 14. The first lumen 304 is configured for delivery of a microcatheter or flow-directed catheter, in order to perform an endovascular procedure. The second lumen 306 is configured for placement of a guidewire, in order to track the guiding catheter 300 to a desired location within the vasculature. The second lumen 306 is also configured for placement of a stylet sheath/dilator 16 and stylet 18. The length along the first lumen 304 and the second lumen 306 extending between the distal orifice 316 and the exit orifice 308 may be between about 0.5 cm and about 30 cm, or between about 15 cm and about 25 cm, or between about 15 cm and about 20 cm. The guiding catheter 300 is thus configured to be used as a single-operator exchange catheter, or a rapid exchange catheter. If a long guiding catheter 300 is desired, to track into very distal arteries, the shorter length of the second lumen 306 allows a shorter stylet 18 and stylet sheath/dilator 16 to be used.

FIG. 23 illustrates a system for accessing arterial vasculature from a venous insertion site 320 comprising the guiding catheter 300 of FIG. 22, along with an outer sheath 322, a stylet sheath/dilator 324 and a stylet 326 having a puncture member 328. The outer sheath 322 is shown in FIG. 23 having a straight distal section, for simplicity, but the outer sheath 322 can be configured to have a curved portion similar to the curved portion 32 of the guiding catheter 14 of FIG. 1, with all of the same utility. Though no proximal hubs are shown in FIG. 23, it is contemplated that proximal hubs described in the prior embodiments may be incorporated. FIG. 26 illustrates that the stylet sheath/dilator 324 resides within the outer sheath 322 and next to the guiding catheter 300 in a proximal section. A proximal portion 307 of the first lumen 304 is visible. FIG. 25 illustrates the stylet sheath/dilator 324 within the second lumen 306. FIG. 24 illustrates the stylet sheath/dilator 324 within a distal portion 305 of the first lumen 304 at a distal section 309. The outer sheath 322, guiding catheter 300, stylet sheath/dilator 324, and stylet 326 may be made with similar materials and dimensions as described in relation to the outer sheath 12, guiding catheter 14, stylet sheath/dilator 16, and stylet 18, except for the dimensions of the two-lumen, "number 8-shape" luminal configuration of the guiding catheter 300. The proximal hubs of the stylet sheath/dilator 324 and stylet 326 may be removable to allow the guiding catheter 300 to be completely removed over the stylet sheath/dilator 324, and stylet 326. A second guiding catheter 300 may then be replaceable and insertable over the stylet sheath/dilator 324 and the stylet 326.

Figure 27:
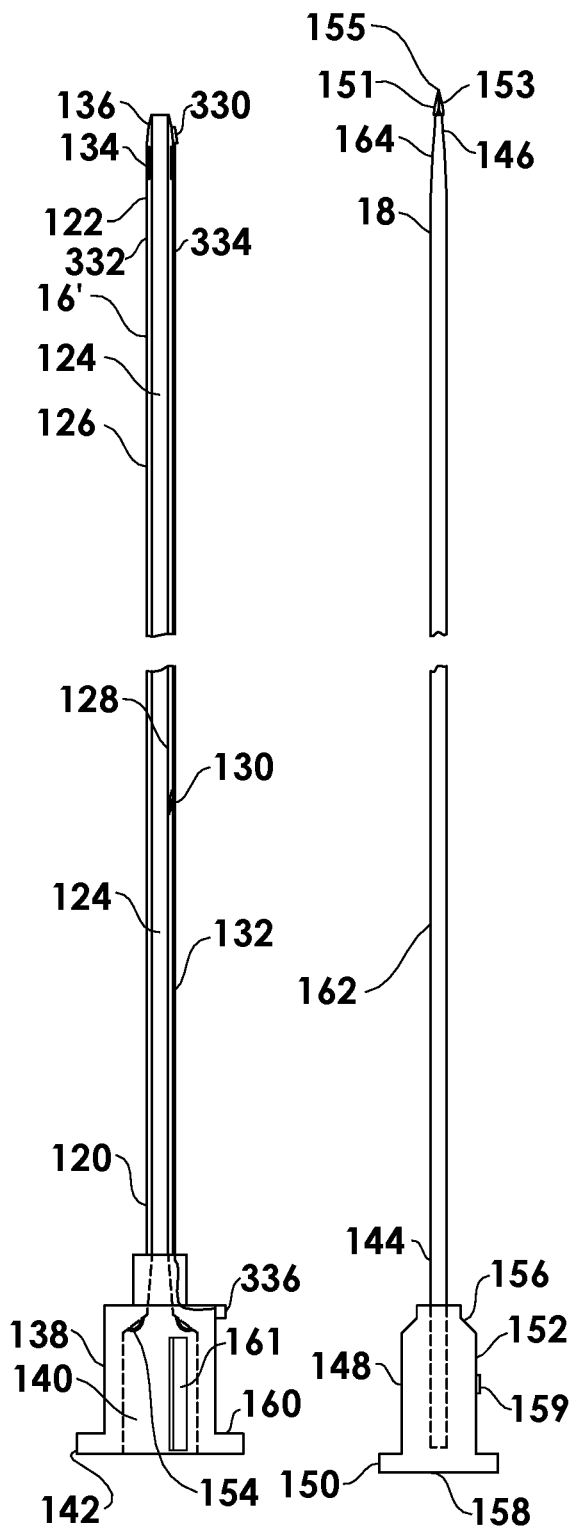
FIG. 27 is a partial sectional view of an alternative stylet sheath/dilator and stylet for the system for accessing arterial vasculature from a venous insertion site of FIG. 1, according to an embodiment of the present disclosure.

FIG. 27 illustrates an alternative stylet sheath/dilator 16' for use with the stylet 18 and the system for accessing arterial vasculature from a venous insertion site 10 of FIG. 1. A sensor 330 is carried on the distal end 122 of the stylet sheath/dilator 16' on an external surface 332 of the tubular body 126. In other embodiments, the sensor 330 may be carried within the lumen 124. One or more wires 334 (conductors) are coupled to the sensor 330 and extend along the tubular body 126 (on the outside, inside, or embedded within), connecting to a proximal connector 336 which may be coupled to a monitor (not shown). The wires 334 may extend substantially longitudinally, or may wind in a helical manner around the tubular body 126. The sensor 330 is configured to measure a characteristic of flow within a blood vessel.

Figure 28:
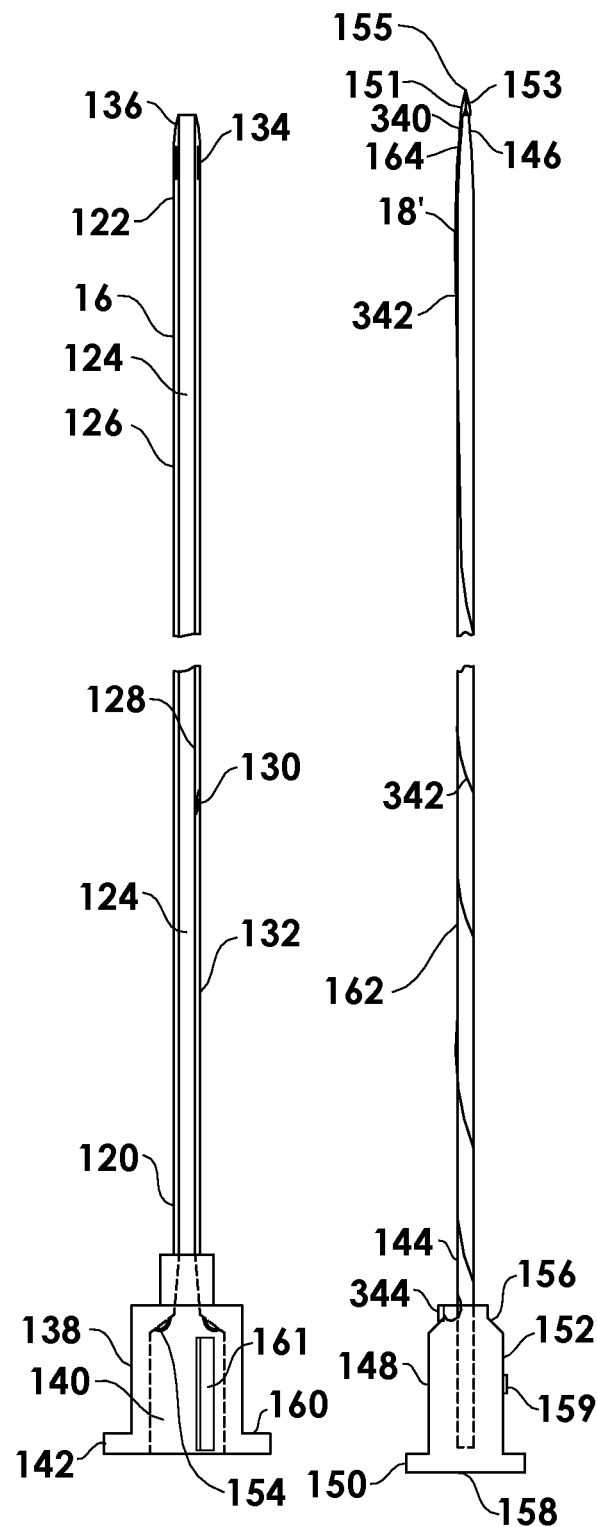
FIG. 28 is a partial sectional view of an alternative stylet sheath/dilator and stylet for the system for accessing arterial vasculature from a venous insertion site of FIG. 1, according to an embodiment of the present disclosure.

FIG. 28 illustrates an alternative stylet 18' for use with the stylet sheath/dilator 16 and the system for accessing arterial vasculature from a venous insertion site 10 of FIG. 1. A sensor 340 is carried on the distal end 146 of the stylet 18'. One or more wires 342 (conductors) are coupled to the sensor 340 and extend along the shaft 162, connecting to a proximal connector 344 which may be coupled to a monitor (not shown). The wires 342 may extend substantially longitudinally, or may wind in a helical manner around the shaft 162. The sensor 340 is configured to measure a characteristic of flow within a blood vessel.

The sensor 330, 340 may comprise a Doppler (ultrasound) sensor, configured to measure a flow velocity. The monitor may be coupled to circuitry that Is configured to calculate a volumetric flow rate from the flow velocity data, and from data input that describes the diameter or other dimensional characteristics of the blood vessel. Ultrasound sensors may be used such as those described in U.S. Pat. No. 4,947,852, issued Aug. 14, 1990, and titled "Apparatus and method for continuously measuring volumetric blood flow using multiple transducer and catheter for use therewith," which is hereby incorporated by reference in its entirety for all purposes. In other embodiments, the sensor 330, 340 may comprise a pressure sensor. Pressure sensors may be used such as those described in U.S. Pat. No. 6,976,965, issued Dec. 20, 2005, and titled "Ultra miniature pressure sensor," or in U.S. Pat. No. 5,226,423, issued Jul. 13, 1993, and titled "Sensor guide construction and use thereof," both of which are hereby incorporated by reference in their entirety for all purposes. In other embodiments, the sensor 330 may be a microphone or other sonic sensor.

Figure 29:
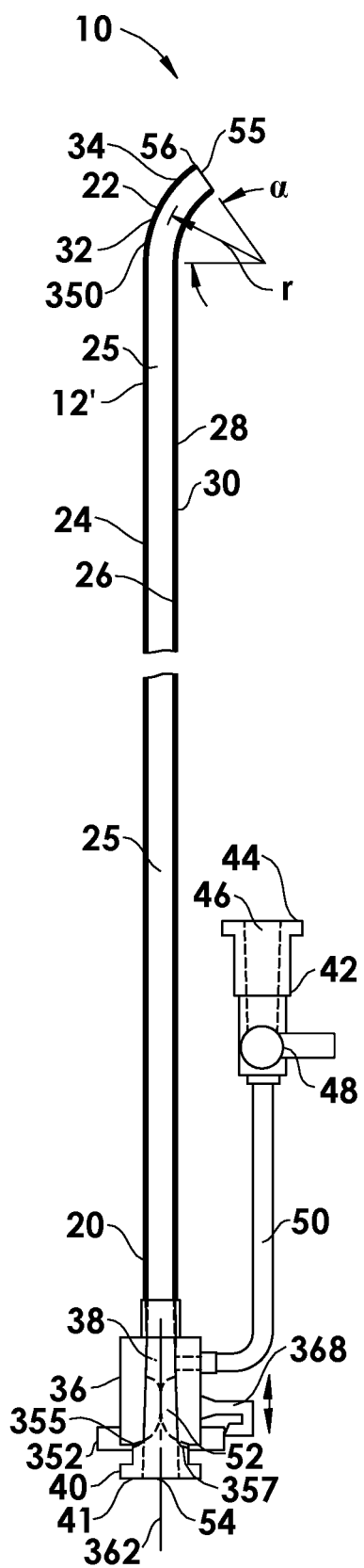
FIG. 29 is a partial sectional view of an alternative curved outer sheath for the system for accessing arterial vasculature from a venous insertion site of FIG. 1, according to an embodiment of the present disclosure.
Figure 30:
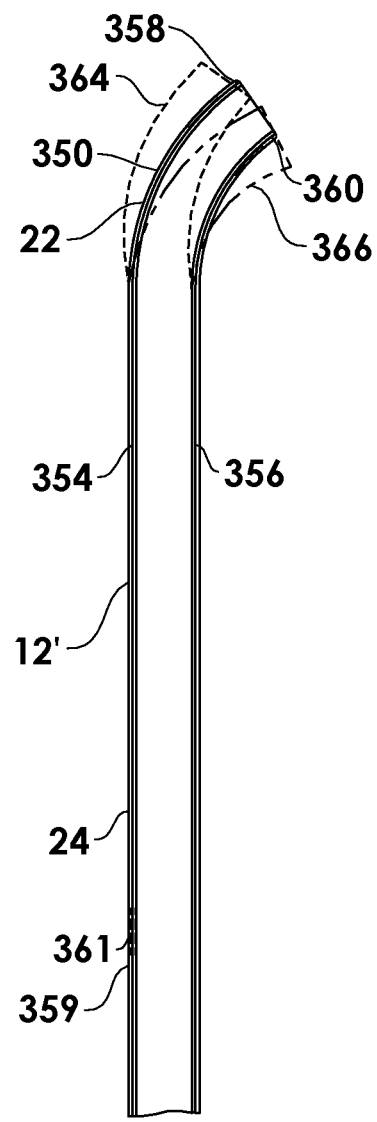
FIG. 30 is a detailed view of the curved distal portion of the curved outer sheath of FIG. 29 including multiple deflected positions.

The measurement of the characteristic of blood flow (flow velocity, volumetric flow rate, blood pressure) by the sensor 330, 340 can be used to sense the location of an artery that is in proximity to a vein inside which the stylet sheath/dilator 16' and stylet 18 (or the stylet 18' and stylet sheath/dilator 16) reside. For example, if the sensor 330, 340 is a Doppler sensor or other sonic sensor, a user may move the stylet sheath/dilator 16' or stylet 18' thus moving the sensor 330 or sensor 340 until the strongest flow signal is received. This helps to indicate the proximity of an artery, because of the significant arterial flow. For example, a Doppler sensor placed within an internal jugular vein may sense am adjacent common carotid artery, and may even sense the nearest possible location of the adjacent common carotid artery. Thus, an optimal puncture and crossing site may be identified. This may be done in conjunction with angiography or fluoroscopy, or in some cases, may be done without angiography or fluoroscopy. In, on the other hand, the sensor 330, 340 is a pressure sensor (or a Doppler sensor), the measured pressure or flow would be expected to significantly increase when the sensor 330, 340 (and thus the tip of the stylet sheath/dilator 16' or stylet 18') crosses through a puncture from the vein to the artery. This allows confirmation of a correct puncture and/or crossing, and may even be able to quantify the disease state of the artery that has been entered. For example, the flow or pressure along the artery may be measured at different longitudinal locations to assess flow and disease state. FIG. 29 illustrates an alternative curved outer sheath 12' for use with the system for accessing arterial vasculature from a venous insertion site 10 of FIG. 1. The distal end 22 includes a deflectable tip 350 which may be deflected in either direction (see FIG. 30) by a control ring 352, which is rotationally carried by the proximal hub 36. The control ring 352 may be rotated around longitudinal axis 362 by a user in a first rotational direction (e.g., clockwise) and a second, opposite rotational direction (e.g., counter-clockwise). The control ring 352 is attached to a first wire 354 and a second wire 356 at their respective proximal ends 355, 357. Each of the first wire 354 and second wire 356 extends through one of two longitudinally-extending lumens 361 in the wall 359 of the tubular body 24. Each wire 354, 356 is secured at their respective distal ends 358, 360 to the distal end 22. Thus, rotation by the user of the control ring 352 in a first direction increases the tension on wire 354 and decreases the tension on wire 356, causing the deflectable tip 350 to move into first position 364. Rotation by the user of the control ring 352 in a second, opposite direction increases the tension on wire 356 and decreases the tension on wire 354, causing the deflectable tip 350 to move into second position 366. In use, the deflectable tip 350 may be deflected by the user until it is in the desired position for puncture and crossing, which may include the first position 364, the second position 366, or any number of positions therebetween. There may even be positions that are more extreme than the first position 364 or the second position 366. In some embodiments, the deflectable tip 350 is configured to be deflected about 20° in each direction, or about 10° in each direction, or about 5° in each direction. In some cases, the control ring 352 may even be used to counteract any straightening the that passage of one or more of the guiding catheter 14, stylet sheath/dilator 16, and/or stylet 18 may attempt to cause. A lock 368 is slideably carried on the proximal hub 36 (double-ended arrow), and is configured to snappingly or frictionally engage and disengage the control ring 352, to restrict or allow its rotation with respect to the proximal hub 36. Thus, the deflectable tip 350 may be maintained in a desired position by the user, by use of the lock 368.

While the foregoing is directed to embodiments of the present disclosure, other and further embodiments may be devised without departing from the basic scope thereof.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method for accessing arterial vasculature from a venous insertion site, comprising:
   providing an elongate crossing member configured to be disposed within a lumen of a guiding catheter for two-way longitudinal movement therein, the guiding catheter having a proximal end and a distal end, the elongate crossing member having a proximal end, a distal end, and a lumen extending between the distal end and an orifice proximal to the distal end, the distal end of the elongate crossing member including a distal tip comprising a frusto-conical outer surface;
   providing a stylet configured to be disposed within the lumen of the elongate crossing member, the stylet configured for two-way longitudinal movement therein, the stylet having a proximal end and a distal end, the distal end of the stylet including a puncturing tip configured to penetrate a venous wall and an arterial wall adjacent the venous wall, wherein the elongate crossing member and the stylet are configured to be placed together with the guiding catheter through a lumen of a sheath having a proximal end, a distal end and a curved distal portion, and wherein the elongate crossing member and the stylet are removable from the lumen of the guiding catheter when the guiding catheter is within the lumen of the sheath with at least the distal end of the guiding catheter extending out of the distal end of the sheath;
   placing the distal end of the sheath into a vein of a subject from a puncture site;
   advancing the sheath such that the distal end of the sheath is positioned adjacent a wall portion of an internal jugular vein;
   advancing the stylet such that the puncturing tip of the stylet penetrates the wall portion of the internal jugular vein and penetrates an adjacent wall portion of a common carotid artery;
   advancing the distal end of the elongate crossing member into the common carotid artery through an opening created the stylet;
   advancing the guiding catheter into the common carotid artery;
   removing the elongate crossing member and the stylet from the guiding catheter; and performing an interventional procedure through the guiding catheter.

2. The method of claim 1, further comprising extending the guiding catheter partially within the internal jugular vein and partially within the common carotid artery.

3. The method of claim 2, further comprising extending the guiding catheter within at least a portion of an internal carotid artery.

4. The method of claim 1, wherein the distal end of the guiding catheter has a generally straight shape.

5. The method of claim 1, wherein the stylet is configured to be inserted through the lumen of the elongate crossing member, and wherein the stylet is configured to be removed from the lumen of the elongate crossing member.

6. The method of claim 1, wherein the elongate crossing member comprises a tubular body comprising a polymeric material.

7. The method of claim 6, wherein the polymeric material is selected from the group consisting of: polyether block amide and polyurethane.

8. The method of claim 1, wherein the distal tip of the elongate crossing member comprises a fillet.

9. The method of claim 1, wherein the proximal end of the stylet is coupled to a hub.

10. The method of claim 1, wherein the orifice of the elongate crossing member is located at the proximal end of the elongate crossing member.

11. A method for accessing arterial vasculature from a venous insertion site, comprising:
providing an elongate crossing member configured to be disposed within a lumen of a guiding catheter for two-way longitudinal movement therein, the guiding catheter having a proximal end and a distal end, the elongate crossing member having a proximal end, a distal end, and a lumen extending between the distal end and an orifice proximal to the distal end, the distal end of the elongate crossing member including a distal tip comprising a fillet;
providing a stylet configured to be disposed within the lumen of the elongate crossing member, the stylet configured for two-way longitudinal movement therein, the stylet having a proximal end and a distal end, the distal end of the stylet including a puncturing tip configured to penetrate a venous wall and an arterial wall adjacent the venous wall, wherein the elongate crossing member and the stylet are configured to be placed together with the guiding catheter through a lumen of a sheath having a proximal end, a distal end and a curved distal portion, and wherein the elongate crossing member and the stylet are removable from the lumen of the guiding catheter when the guiding catheter is within the lumen of the sheath with at least the distal end of the guiding catheter extending out of the distal end of the sheath;
placing the distal end of the sheath into a vein of a subject from a puncture site;
advancing the sheath such that the distal end of the sheath is positioned adjacent a wall portion of an internal jugular vein;
advancing the stylet such that the puncturing tip of the stylet penetrates the wall portion of the internal jugular vein and penetrates an adjacent wall portion of a common carotid artery;
advancing the distal end of the elongate crossing member into the common carotid artery through an opening created by the stylet;

advancing the guiding catheter into the common carotid artery;
removing the elongate crossing member and the stylet from the guiding catheter; and
performing an interventional procedure through the guiding catheter.

12. The method of claim 11, further comprising extending the guiding catheter partially within the internal jugular vein and partially within the common carotid artery.

13. The method of claim 12, further comprising extending the guiding catheter within at least a portion of an internal carotid artery.

14. The method of claim 11, wherein the distal end of the guiding catheter has a generally straight shape.

15. The method of claim 11, wherein the stylet is configured to be inserted through the lumen of the elongate crossing member, and wherein the stylet is configured to be removed from the lumen of the elongate crossing member.

16. The method of claim 11, wherein the elongate crossing member comprises a tubular body comprising a polymeric material.

17. The method of claim 16, wherein the polymeric material is selected from the group consisting of: polyether block amide and polyurethane.

18. The method of claim 11, wherein the proximal end of the stylet is coupled to a hub.

19. The method of claim 11, wherein the orifice of the elongate crossing member is located at the proximal end of the elongate crossing member.

20. A method for accessing arterial vasculature from a venous insertion site, comprising:
providing a system for accessing arterial vasculature from a venous insertion site, the system comprising:
a sheath having a proximal end, a distal end, a lumen extending therebetween, and a curved distal portion;
a guiding catheter configured to be disposed within the lumen of the sheath for two-way longitudinal movement therein, the guiding catheter having a proximal end, a distal end, and a lumen extending therebetween;
an elongate crossing member configured to be disposed within the lumen of the guiding catheter for two-way longitudinal movement therein, and having a proximal end, a distal end, and a lumen extending between the distal end and an orifice proximal to the distal end, the distal end of the elongate crossing member including a distal tip comprising one or both of: a frusto-conical outer surface and/or a fillet; and
a stylet configured to be disposed within the lumen of the elongate crossing member, the stylet configured for two-way longitudinal movement therein, the stylet having a proximal end and a distal end, the distal end of the stylet including a puncturing tip configured to penetrate a venous wall and an arterial wall adjacent the venous wall,
wherein placement of the guiding catheter, the elongate crossing member, and the stylet together through the lumen of the sheath at the curved distal portion does not substantially straighten the curved distal portion, and wherein the elongate crossing member and the stylet are removable from the lumen of the guiding catheter when the guiding catheter is within the lumen of the sheath with at least the distal end of the guiding catheter extending out of the distal end of the sheath;
placing the distal end of the sheath into a vein of a subject from a puncture site;

advancing the sheath such that the distal end of the sheath is positioned adjacent a wall portion of an internal jugular vein;

advancing the stylet such that the puncturing tip of the stylet penetrates the wall portion of the internal jugular vein and penetrates an adjacent wall portion of a common carotid artery;

advancing the distal end of the elongate crossing member into the common carotid artery through an opening created by the stylet;

advancing the guiding catheter into the common carotid artery;

removing the elongate crossing member and the stylet from the guiding catheter; and performing an interventional procedure through the guiding catheter.

* * * * *

UNITED STATES PATENT AND TRADEMARK OFFICE
CERTIFICATE OF CORRECTION

| | |
|---|---|
| PATENT NO. | : 11,389,194 B2 |
| APPLICATION NO. | : 16/594984 |
| DATED | : July 19, 2022 |
| INVENTOR(S) | : Ansaar T. Rai et al. |

It is certified that error appears in the above-identified patent and that said Letters Patent is hereby corrected as shown below:

In the Claims

Column 22, Claim 1, Line 39: insert -- by -- before "the stylet"

Signed and Sealed this
Twentieth Day of December, 2022

*Katherine Kelly Vidal*

Katherine Kelly Vidal
*Director of the United States Patent and Trademark Office*